(12) United States Patent
Faller et al.

(10) Patent No.: US 9,724,120 B2
(45) Date of Patent: Aug. 8, 2017

(54) CLAMP ARM FEATURES FOR ULTRASONIC SURGICAL INSTRUMENT

(71) Applicant: Ethicon Endo-Surgery, Inc., Cincinnati, OH (US)

(72) Inventors: Craig N. Faller, Milford, OH (US); Patrick A. Weizman, Cincinnati, OH (US); Jacqueline A. Anim, Clayton, OH (US); John W. Willis, Cincinnati, OH (US); Thomas C. Gallmeyer, Cincinnati, OH (US); Samardh Onukuri, Cincinnati, OH (US); John B. Schulte, West Chester, OH (US); Amy L. Marcotte, Mason, OH (US); Sean P. Conlon, Loveland, OH (US); Jacob S Gee, Cincinnati, OH (US); Kevin L. Houser, Springboro, OH (US); Jeffrey L. Aldridge, Lebanon, OH (US); Ryan M. Asher, Cincinnati, OH (US); Foster B. Stulen, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 210 days.

(21) Appl. No.: 14/109,190

(22) Filed: Dec. 17, 2013

(65) Prior Publication Data
US 2015/0164532 A1     Jun. 18, 2015

(51) Int. Cl.
*A61B 17/32* (2006.01)
*A61B 17/28* (2006.01)
(Continued)

(52) U.S. Cl.
CPC .... *A61B 17/320092* (2013.01); *A61B 17/282* (2013.01); *A61B 2017/0088* (2013.01);
(Continued)

(58) Field of Classification Search
CPC ............ A61B 17/32; A61B 17/320092; A61B 17/320068; A61B 2017/00738;
(Continued)

(56) References Cited

U.S. PATENT DOCUMENTS

| 4,526,839 A | 7/1985 | Herman et al. |
| 5,322,055 A | 6/1994 | Davison et al. |

(Continued)

FOREIGN PATENT DOCUMENTS

| EP | 0477585 A2 | 4/1992 |
| EP | 0908149 A1 | 4/1999 |

(Continued)

OTHER PUBLICATIONS

Non-Provisional Patent Application No. U.S. Appl. No. 13/657,553, filed Oct. 22, 2012.

(Continued)

*Primary Examiner* — Victor Nguyen
(74) *Attorney, Agent, or Firm* — Frost Brown Todd LLC

(57) ABSTRACT

A surgical apparatus includes an end effector having an ultrasonic blade, a clamp arm, and a clamp pad. The end effector applies ultrasonic energy at the blade. The clamp arm pivots relative to the blade. The clamp pad is positioned on the clamp arm adjacent to the blade. The clamp arm includes a latching feature to retain the clamp pad relative to the clamp arm to prevent the clamp pad from moving laterally, longitudinally, and perpendicularly relative to the clamp arm.

17 Claims, 39 Drawing Sheets

(51) Int. Cl.
*A61B 17/00* (2006.01)
*A61B 17/29* (2006.01)

(52) U.S. Cl.
CPC .......... *A61B 2017/00353* (2013.01); *A61B 2017/00477* (2013.01); *A61B 2017/00526* (2013.01); *A61B 2017/00738* (2013.01); *A61B 2017/00853* (2013.01); *A61B 2017/00995* (2013.01); *A61B 2017/2825* (2013.01); *A61B 2017/2926* (2013.01); *A61B 2017/2945* (2013.01); *A61B 2017/320044* (2013.01); *A61B 2017/320072* (2013.01)

(58) Field of Classification Search
CPC .......... A61B 18/1206; A61B 17/282; A61B 17/3203; A61B 17/00995
See application file for complete search history.

(56) References Cited

U.S. PATENT DOCUMENTS

| | | | |
|---|---|---|---|
| 5,810,881 A | 9/1998 | Hoskin et al. | |
| 5,873,873 A | 2/1999 | Smith et al. | |
| 5,980,510 A | 11/1999 | Tsonton et al. | |
| 6,004,335 A | 12/1999 | Vaitekunas et al. | |
| 6,193,709 B1 | 2/2001 | Miyawaki et al. | |
| 6,206,896 B1 | 3/2001 | Howell et al. | |
| 6,325,811 B1 | 12/2001 | Messerly | |
| 6,500,176 B1 | 12/2002 | Truckai et al. | |
| 6,773,444 B2 | 8/2004 | Messerly | |
| 6,783,524 B2 | 8/2004 | Anderson et al. | |
| 6,821,284 B2 | 11/2004 | Sturtz et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,416,101 B2 | 8/2008 | Shelton, IV et al. | |
| 7,780,659 B2 | 8/2010 | Okada et al. | |
| 8,453,914 B2 | 6/2013 | Laurent et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,814,895 B2 | 8/2014 | Messerly | |
| 8,968,358 B2 | 3/2015 | Reschke | |
| 9,113,943 B2 | 8/2015 | Ross et al. | |
| 9,149,292 B2 | 10/2015 | Sawada et al. | |
| 9,326,787 B2 | 5/2016 | Sanai et al. | |
| 2003/0114874 A1 | 6/2003 | Craig et al. | |
| 2003/0236537 A1 | 12/2003 | Hart et al. | |
| 2005/0198839 A1* | 9/2005 | Walker | B26B 21/225 30/527 |
| 2006/0079874 A1* | 4/2006 | Faller | A61B 17/32009 606/40 |
| 2006/0079879 A1 | 4/2006 | Faller et al. | |
| 2007/0016236 A1 | 1/2007 | Beaupre | |
| 2007/0191713 A1 | 8/2007 | Eichmann et al. | |
| 2007/0282333 A1 | 12/2007 | Fortson et al. | |
| 2008/0103494 A1 | 5/2008 | Rioux et al. | |
| 2008/0200940 A1 | 8/2008 | Eichmann et al. | |
| 2009/0209990 A1 | 8/2009 | Yates et al. | |
| 2010/0063527 A1 | 3/2010 | Beaupre et al. | |
| 2010/0069940 A1 | 3/2010 | Miller et al. | |
| 2011/0087212 A1 | 4/2011 | Aldridge et al. | |
| 2011/0087218 A1 | 4/2011 | Boudreaux et al. | |
| 2012/0078243 A1 | 3/2012 | Worrell et al. | |
| 2012/0078247 A1 | 3/2012 | Worrell et al. | |
| 2012/0078249 A1 | 3/2012 | Eichmann et al. | |
| 2012/0112687 A1 | 5/2012 | Houser et al. | |
| 2012/0116265 A1 | 5/2012 | Houser et al. | |
| 2012/0116379 A1 | 5/2012 | Yates et al. | |
| 2013/0023868 A1 | 1/2013 | Worrell et al. | |
| 2013/0030428 A1 | 1/2013 | Worrell et al. | |
| 2013/0096468 A1* | 4/2013 | Rhee | A61B 17/32009 601/2 |
| 2013/0103023 A1 | 4/2013 | Monson et al. | |
| 2014/0005701 A1 | 1/2014 | Olson et al. | |

FOREIGN PATENT DOCUMENTS

| | | |
|---|---|---|
| EP | 1433428 A1 | 6/2004 |
| EP | 2113210 A2 | 11/2009 |
| JP | 2004-267445 A | 9/2004 |
| WO | WO 2014/004120 A1 | 1/2014 |
| WO | WO 2014/004248 A1 | 1/2014 |
| WO | WO 2014/052809 A1 | 4/2014 |

OTHER PUBLICATIONS

Non-Provisional Patent Application No. U.S. Appl. No. 13/716,308, filed Dec. 17, 2012.
Non-Provisional Patent Application No. U.S. Appl. No. 14/028,717, filed Sep. 17, 2013.
U.S. Appl. No. 61/410,603, filed Nov. 5, 2010.
International Search Report dated Apr. 22, 2015 fo Application No. PCT/US2014/069033, 12 pgs.
International Preliminary Report on Patentability and Written Opinion dated Jun. 21, 2016 for Application No. PCT/US2014/069033, 16 pgs.

* cited by examiner

CLAMP ARM FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, the disclosure of which is incorporated by reference herein; U.S. Pub. No. 2010/0069940, entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011, the disclosure of which is incorporated by reference herein; and U.S. Pub. No. 2012/0029546, entitled "Ultrasonic Surgical Instrument Blades," published Feb. 2, 2012, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," the disclosure of which is incorporated by reference herein; and U.S. patent application Ser. No. 13/657,553, filed Oct. 22, 2012, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
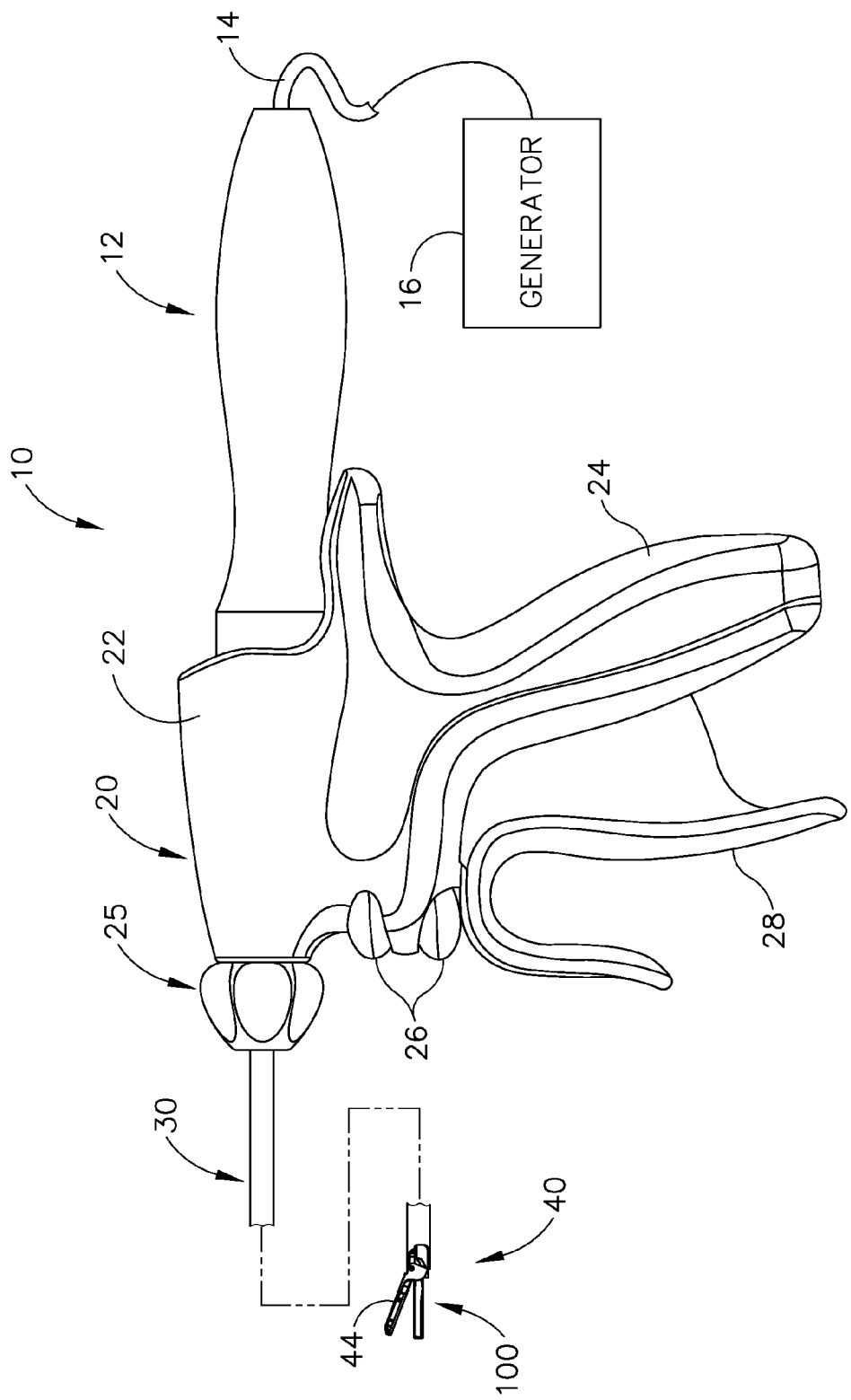
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10) that is configured to be used in a minimally invasive surgical procedure (e.g., via a trocar or other small diameter access port, etc.). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750; U.S. Pub. No. 2010/0069940; U.S. Pub. No. 2011/0015660; U.S. Pub. No. 2012/0112687; U.S. Pub. No. 2012/0116265; U.S. patent application Ser. Nos. 13/538,588; 13/657,553; U.S. Pat. App. No. 61/410,603; and/or U.S. patent application Ser. No. 14/028,717. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2A:
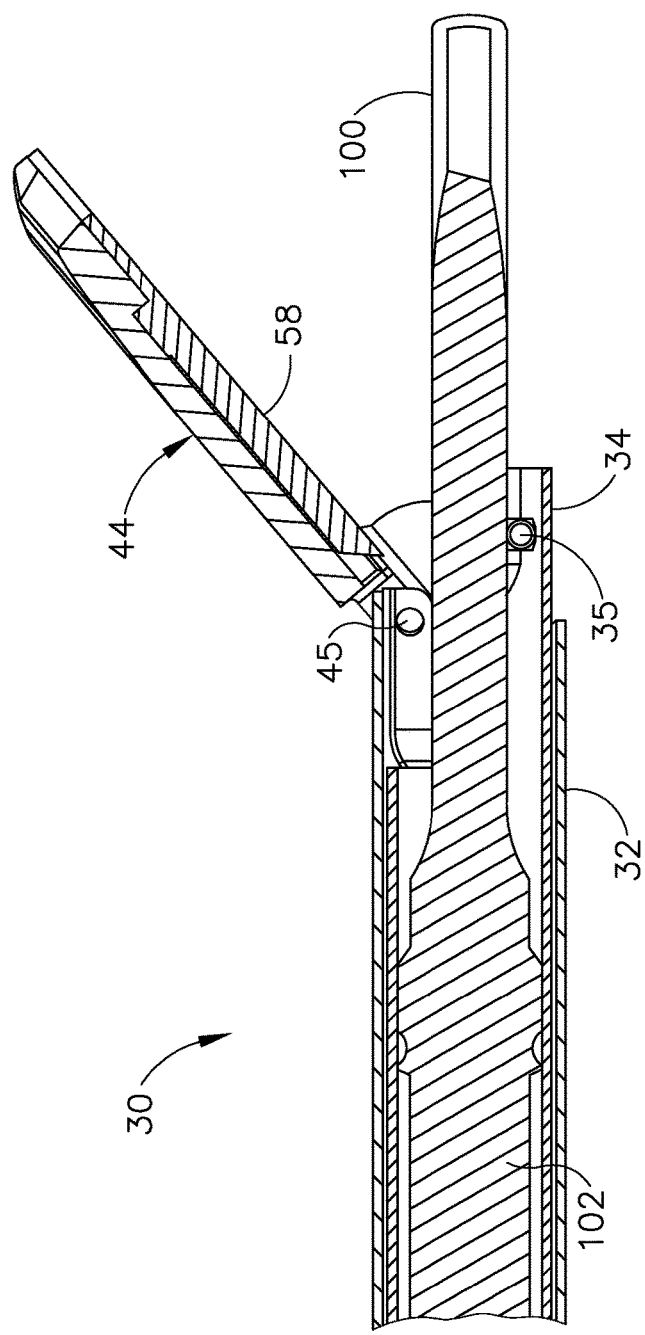
FIG. 2A depicts a side elevational view of an end effector of the instrument of FIG. 1 in an open position.
Figure 2B:
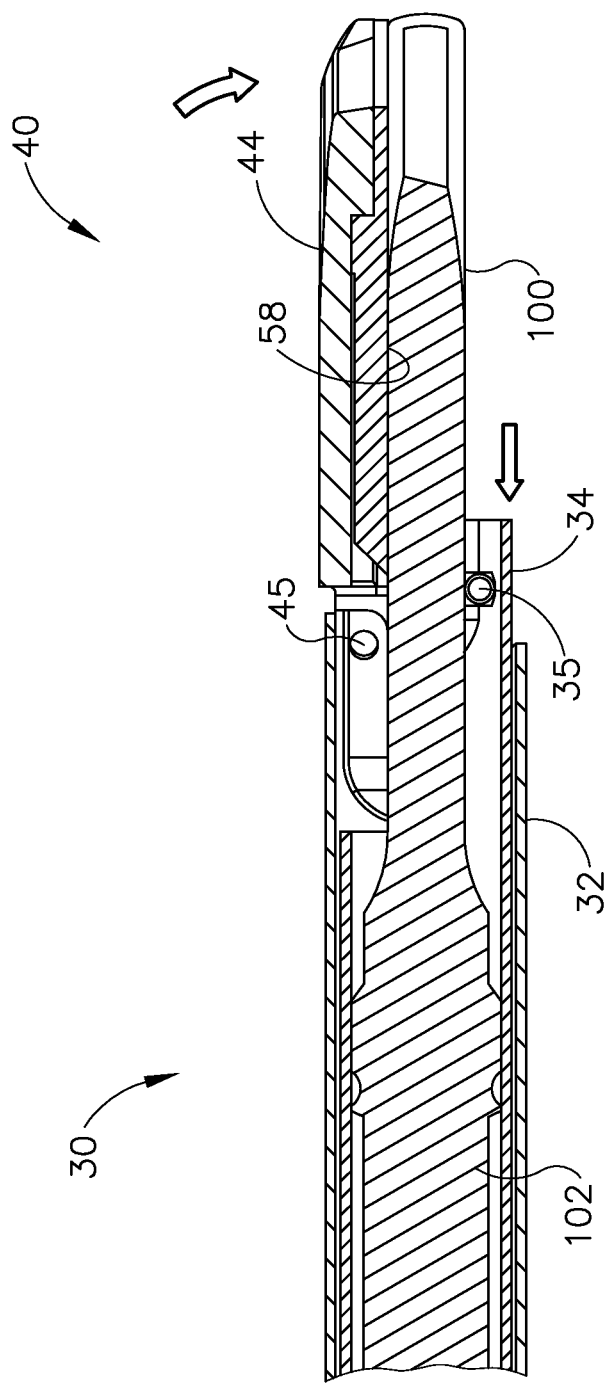
FIG. 2B depicts a side elevational view of the end effector of FIG. 2A in a closed position.

Instrument (10) of the present example comprises an end effector (40), a shaft assembly (30), and a handle assembly (20). End effector (40) comprises an ultrasonic blade (100) and a clamp arm (44) that is pivotable toward and away from ultrasonic blade (100) to thereby clamp tissue between clamp arm (44) and ultrasonic blade (100) to cut and/or seal the tissue. End effector (40) is coupled with handle assembly (20) via shaft assembly (30). As shown in FIGS. 2A-2B, shaft assembly (30) comprises an outer sheath (32), an inner tube (34) slidably disposed within outer sheath (32), and a waveguide (102) disposed within inner tube (34). As will be discussed in more detail below, longitudinal translation of inner tube (34) causes actuation of clamp arm (44) at end effector (40).

As best seen in FIG. 2B, a distal end of inner tube (34) is rotatably coupled with a proximal end of clamp arm (44) below ultrasonic blade (100) via a pair of pins (35) that are integral with clamp arm (44), such that longitudinal translation of inner tube (34) relative to outer sheath (32) and handle assembly (20) causes rotation of clamp arm (44) about pin (45) toward and away from ultrasonic blade (100) to thereby clamp tissue between clamp arm (44) and ultrasonic blade (100) to cut and/or seal the tissue. In particular, proximal longitudinal translation of inner tube (34) relative to outer sheath (32) and handle assembly (20) causes clamp arm (44) to move toward ultrasonic blade (100); and distal longitudinal translation of inner tube (34) relative to outer sheath (32) and handle assembly (20) causes clamp arm (44) to move away from ultrasonic blade (100).

Clamp arm (44) includes a clamp pad (58) mounted on clamp arm (44) for cooperation with blade (100). For example, pivotal movement of the clamp arm (44) positions clamp pad (58) in a substantially parallel relationship to, and in contact with, blade (100) or tissue against blade (100) to thereby define a tissue compression region, as shown in FIG. 2B. By this construction, tissue is clamped and compressed between clamp pad (58) and blade (100). When blade (100) is in a non-activated state, clamp pad (58) and blade (100) may cooperate to provide simple tissue grasping. When blade (100) is in an activated state as described in greater detail below, clamp pad (58) and blade (100) may sever and/or seal tissue compressed between clamp pad (58) and blade (100).

Figure 3A:
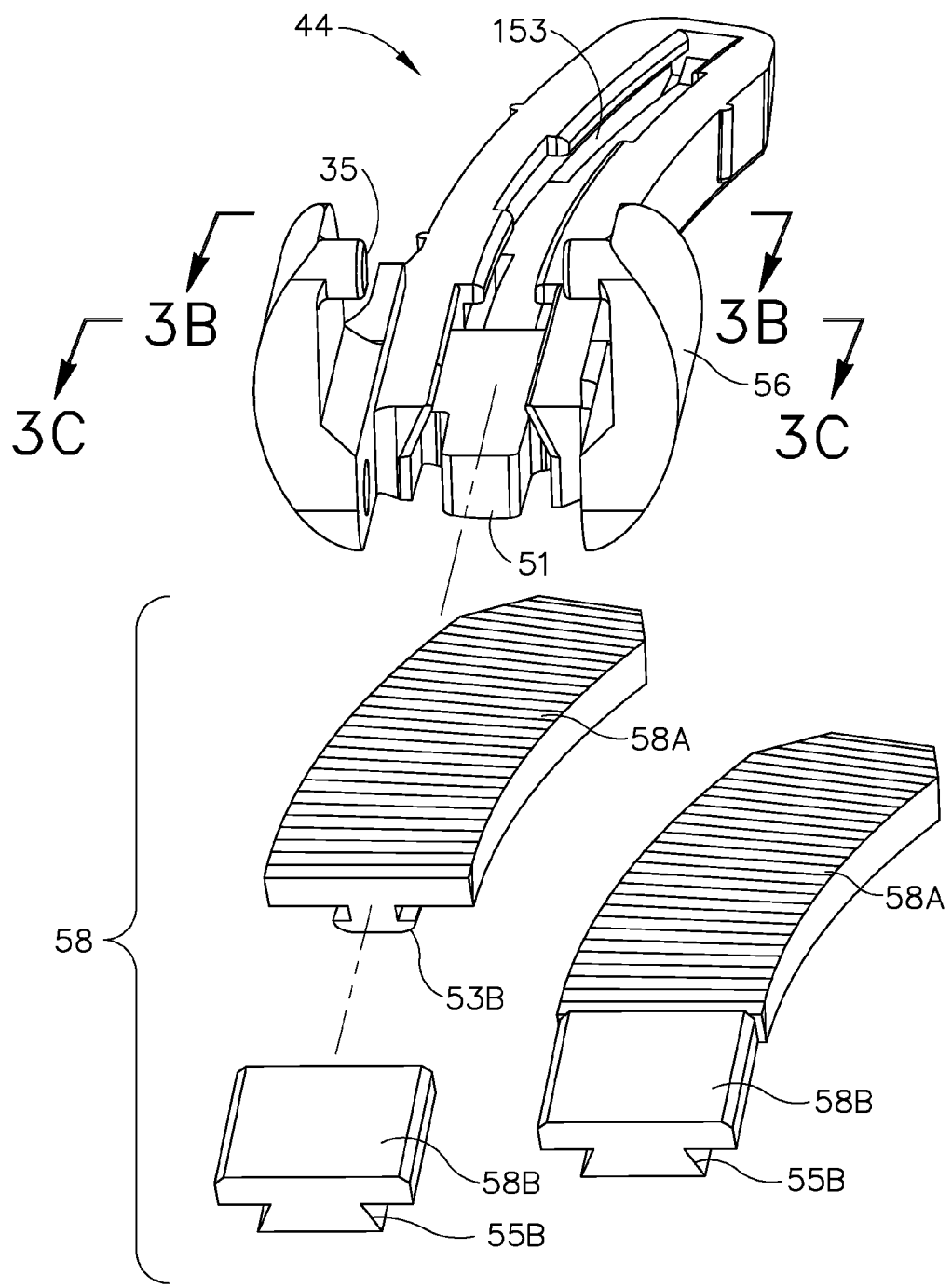
FIG. 3A depicts an exploded perspective view of a clamp arm assembly of the end effector of FIG. 2A, showing the underside of the clamp arm assembly.

FIG. 3A shows the side of clamp pad (58) that faces blade (100). As shown, clamp pad (58) of this example includes a distal portion (58A) with a non-smooth surface, such as a sawtooth-like configuration to enhance the gripping of tissue in cooperation with blade (100). The sawtooth-like configuration, or teeth, provide traction against the movement of blade (100). Of course, the sawtooth-like configuration is just one example of many tissue engaging surfaces to prevent movement of the tissue relative to the movement of blade (100). Other suitable configurations for distal portion (58A) of clamp pad (58) will be apparent to one with ordinary skill in the art in view of the teachings herein. For example, distal portion (58A) may include bumps, crisscross patterns, tread patterns, a bead or sand blasted surface, etc.

Clamp pad (58) further includes a proximal portion (58B) that is smoother than distal portion (58A), such that proximal portion (58B) may be devoid of saw-tooth-like teeth or other tissue traction surfaces. Utilizing a smooth proximal portion (58B) on clamp pad (58) allows tissue in the proximal region to move distally, following the vibratory motion of blade (100), to the more active region of the blade (100). During operation, the tissue in the proximal region of end effector (40) (area of portion (58B)) may desiccate and become thinner; and the distal portion of end effector (40) (area of distal portion (58A)) may transect tissue in that distal region, thereby allowing the desiccated and thin tissue within the proximal region to slide distally into the more active region of end effector (40) to complete the tissue transaction. Clamp pad (58) may be made with polytetrafluoroethylene (PTFE) or any other suitable low-friction material. Clamp pad (58) may be formed in a single piece; or clamp pad (58) may be formed by two separate pieces. Various illustrative variations of clamp pad (58) will be described in greater detail below, while still other suitable configurations for clamp pad (58) will be apparent to one with ordinary skill in the art in view of the teachings herein.

Figure 3B:
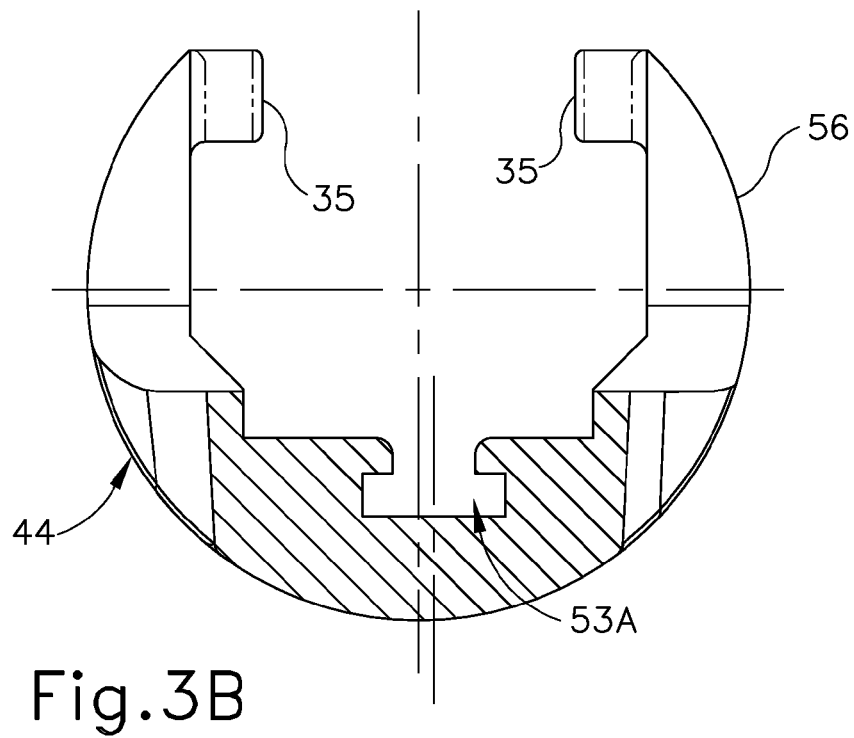
FIG. 3B depicts a cross sectional view of the clamp arm of FIG. 3A taken along line 3B-3B of FIG. 3A.
Figure 3C:
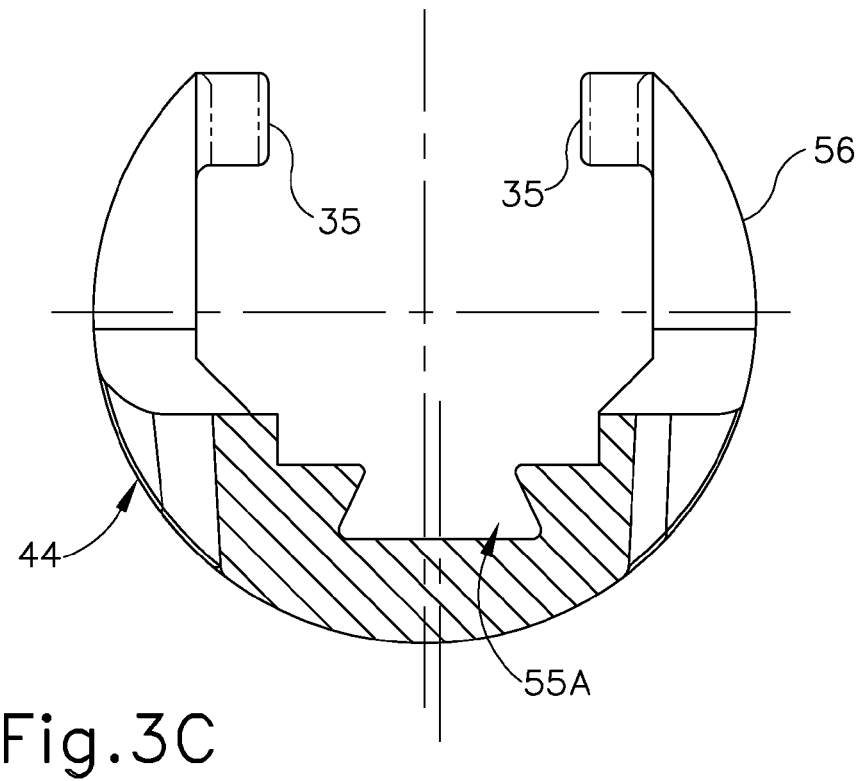
FIG. 3C depicts a cross sectional view of the clamp arm of FIG. 3A taken along line 3C-3C of FIG. 3A.

As shown in FIGS. 3A-3C, clamp arm (44) has different shaped slots (53a, 55a) for accepting clamp pad (58). This configuration may prevent mis-loading of clamp pad (58) and assure that clamp pad (58) is loaded at the correct location within clamp arm (44). For example, clamp arm (44) comprises a distal T-shaped slot (53a) for accepting a T-shaped flange (53B) of distal portion (58A) of clamp pad (58); and a proximal wedged-shaped or dove tailed-shaped slot (55a) for accepting a wedge-shaped flange (55B) of proximal portion (58B) of clamp pad (58). Clamp pad (58) may be inserted into clamp arm (44) by placing pad (58) within clamp arm (44) and then clamping clamp arm (44) down to snap flanges (53B, 55B) of pad (58) within slots (53a, 53b) to secure pad (58) to clamp arm (44). Tab stop (51) engages the proximal end of proximal clamp pad (58B) to secure clamp pad (58) onto clamp arm (44). It should be noted that flanges (53B, 55B) and corresponding slots (53a, 55a) may have alternate shapes and sizes to secure clamp pad (58) to clamp arm (44). Further, other tab stops (51) are possible and may employ various techniques for mechanically attaching clamp pad (58) to clamp arm (44), such as rivets, glue, press fit, etc.

Clamp arm (44) is pivoted relative to blade (100) by actuating handle assembly (20). Referring back to FIG. 1, handle assembly (20) comprises a body (22) including a pistol grip (24), a pair of buttons (26), and a trigger (28) that is pivotable toward and away from pistol grip (24). In the present example, pivoting of trigger (28) toward pistol grip (24) causes clamp arm (44) to move toward ultrasonic blade (100); and pivoting of trigger (28) away from pistol grip (24) causes clamp arm (44) to move away from ultrasonic blade (100). It should be understood, however, that various other suitable configurations may be used.

Figure 4:
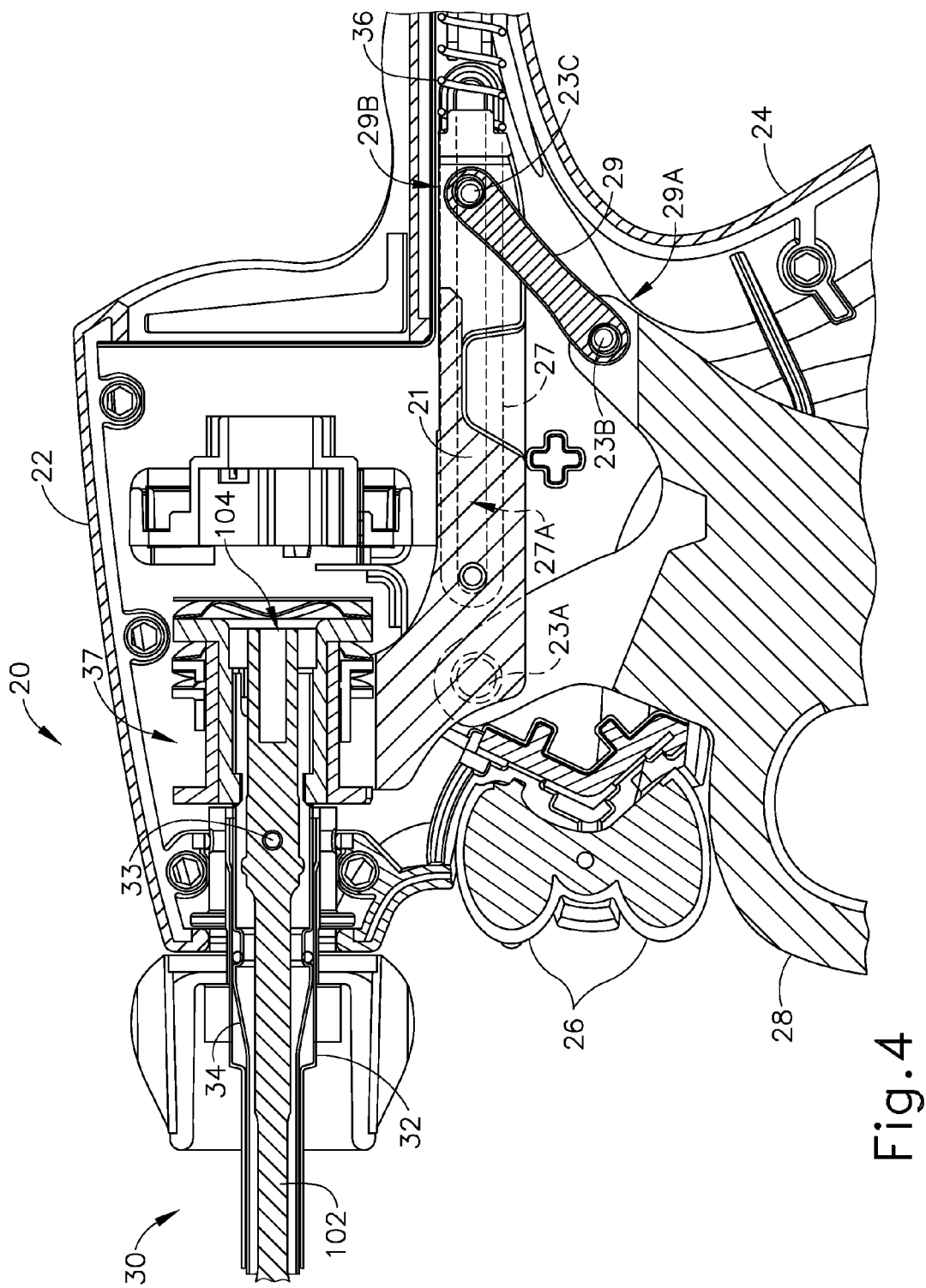
FIG. 4 depicts a cross-sectional view of a handle assembly of the instrument of FIG. 1.

As shown in FIG. 4, trigger (28) is pivotably coupled to handle assembly (20) via a pin (23A) such that trigger (28) rotates about an axis located below shaft assembly (30). Trigger (28) is coupled with a yoke (21) via a linkage (29) such that rotation of trigger (28) about pin (23A) causes longitudinal translation of yoke (21). A first end (29A) of linkage (29) is rotatably coupled with a proximal portion of trigger (28) via a pin (23B). A second end (29B) of linkage (29) is rotatably coupled with a proximal portion of yoke (26) via a pin (23C). A pair of elongate oval-shaped projections (27) extends inwardly from interior surfaces of body (22). An interior surface of each oval-shaped projection (27) defines an elongate oval-shaped slot (27A). Pin (23C) passes completely through the proximal portion of yoke (26) and second end (29B) of linkage (29) such that ends of pin (23C) extend from opposite sides of yoke (26). These ends of pin (23C) are slidably and rotatably disposed within oval-shaped slots (27A). A pin (23D) passes completely through a distal portion of yoke (26) such that ends of pin (23D) extend from opposite sides of yoke (21). These ends of pin (23D) are slidably and rotatably disposed within oval-shaped slots (27A). It should therefore be understood that yoke (21) is longitudinally translatable via pins (23C, 23D) within oval-shaped slots (27A) between a proximal longitudinal position and a distal longitudinal position. Furthermore, because the proximal portion of trigger (28) is coupled with yoke (21) via linkage (29), it should be understood that pivoting of trigger (28) toward pistol grip (24) will cause proximal longitudinal translation of yoke (21) within oval-shaped slots (27A); and that pivoting of trigger (28) away from pistol grip (24) will cause distal longitudinal translation of yoke (21) within oval-shaped slots (27A).

A distal portion of yoke (21) is coupled with inner tube (34) of shaft assembly (30) via a coupling assembly (37). As discussed above, inner tube (34) is longitudinally translatable within outer sheath (32). It should therefore be understood that inner tube (34) is configured to longitudinally translate concomitantly with yoke (21). Furthermore, because pivoting of trigger (28) toward pistol grip (24) causes proximal longitudinal translation of yoke (21), it should be understood that pivoting of trigger (28) toward pistol grip (24) will cause proximal longitudinal translation of inner tube (34) relative to outer sheath (32) and handle assembly (20). Finally, because pivoting of trigger (28) away from pistol grip (24) causes distal longitudinal translation of yoke (21), it should be understood that and that pivoting of trigger (28) away from pistol grip (24) will cause distal longitudinal translation of inner tube (34) relative to outer sheath (32) and handle assembly (20). As shown in FIG. 4, a spring (36) is positioned within a proximal end of body (22) of handle assembly (20). Spring (36) bears distally against a portion of body (22) and a proximal end of yoke (21) to thereby bias yoke (21) toward the distal position. Biasing of yoke (21) toward the distal position causes inner tube (34) to be biased distally and further causes trigger (28) to be biased away from pistol grip (24). Clamp arm (44) is thus resiliently biased to the open position shown in FIG. 2A.

As shown in FIG. 1, an ultrasonic transducer assembly (12) extends proximally from body (22) of handle assembly (20). As will be discussed in more detail below, transducer assembly (12) receives electrical power from generator (16) and converts that power into ultrasonic vibrations through piezoelectric principles as will be described in greater detail below. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Figure 5:
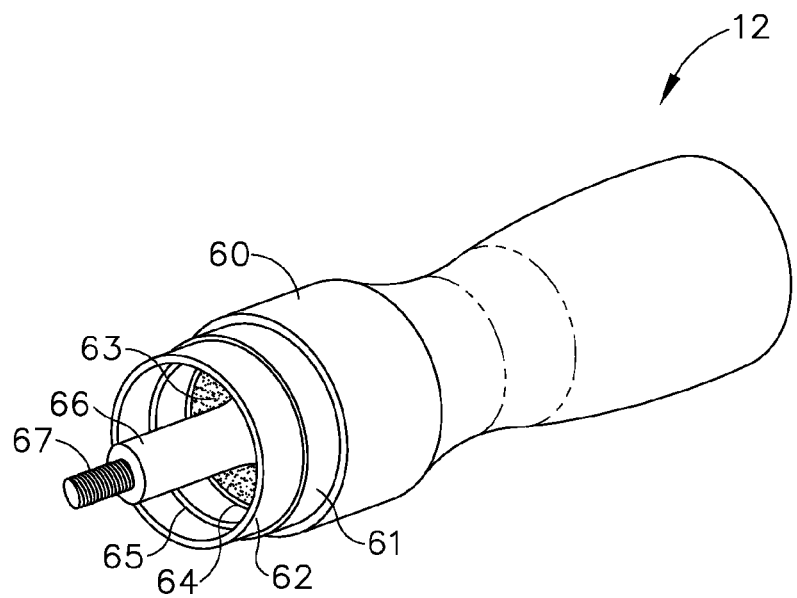
FIG. 5 depicts a perspective view of an exemplary transducer assembly of the instrument of FIG. 1.

As shown in FIG. 1, transducer assembly (12) of the present example is a tubular component that is coupled to generator (16) via cable (14), though it should be understood that transducer assembly (12) may receive power from a source that is integral with instrument (10) such that transducer assembly (12) is cordless. As shown in FIG. 5, the transducer assembly (12) of the present example includes a housing (60), which is acoustically isolated from ultrasonically vibrating elements of transducer assembly (12). The distal end of transducer assembly (12) includes a first conductive ring (65) and a second conductive ring (64), which are both disposed within housing (60) of transducer assembly (12). First conductive ring (65) comprises a ring member that is disposed between housing (60) and a horn (66), which extends distally from housing (60). Horn (66) comprises a threaded stud (67) extending distally therefrom such that horn (66) may be threadably coupled with a threaded bore (104) formed in a proximal end of waveguide (102) (see FIG. 4). First conductive ring (65) is formed adjacent to, or as part of a flange (61) within a transducer cavity (62) such that first conductive ring (65) is electrically isolated from second conductive ring (64) and other conductive components of transducer assembly (12). First conductive ring (65) is located on a non-conductive platform extending distally from housing (60). First conductive ring (65) is electrically coupled to a cable, such as cable (14) shown in FIG. 1, by one or more electrical wires or conductive etchings (not shown) within housing (60).

Second conductive ring (64) of transducer assembly (12) similarly comprises a ring member that is disposed between housing (60) and horn (66). Second conductive ring (64) is disposed between first conductive ring (65) and horn (66). As is shown in FIG. 5, first and second conductive rings (64, 65) are concentric members that are longitudinally offset from each other, with conductive ring (65) also being positioned at a greater radial distance from the central axis shared by conductive rings (64, 65). Second conductive ring (64) is likewise electrically isolated from first conductive ring (65) and other conductive components of transducer assembly (12). Similar to first conductive ring (65), second conductive ring (64) extends from the non-conductive platform. One or more washer-shaped spacers (63) may be disposed between first and second conductive rings (64, 65) or between the rings (64, 65) and other members of transducer assembly (12). Second conductive ring (64) is also electrically coupled to a cable, such as cable (14) shown in FIG. 1, by one or more electrical wires or conductive etchings (not shown) within housing (60). One merely exemplary suitable ultrasonic transducer assembly (12) is Model No. HP054, sold by Ethicon Endo-Surgery, Inc. of Cincinnati, Ohio.

As previously discussed, the distal end of transducer assembly (12) threadably couples with a threaded bore (104) formed in the proximal end of waveguide (102) via threaded stud (67) of horn (66). The distal end of transducer assembly (12) also interfaces with one or more electrical connections (not shown) via first and second conductive rings (64, 65) to electrically couple transducer assembly (12) to buttons (26) to provide a user with finger-activated controls for activating transducer assembly (12) while using surgical instrument (10). In some variations, first and second conductive rings (64, 65) may be omitted from the distal end of transducer assembly (12) and the electrical coupling of transducer assembly (12) to buttons (126) may be accomplished by alternative structures, such as conductors at the proximal end of transducer assembly (12), conductors located along the side of housing (60) of transducer assembly (12), directly from cable (14), and/or any other structures and configurations as will be apparent to one of ordinary skill in the art in view of the teachings herein.

Figure 6:
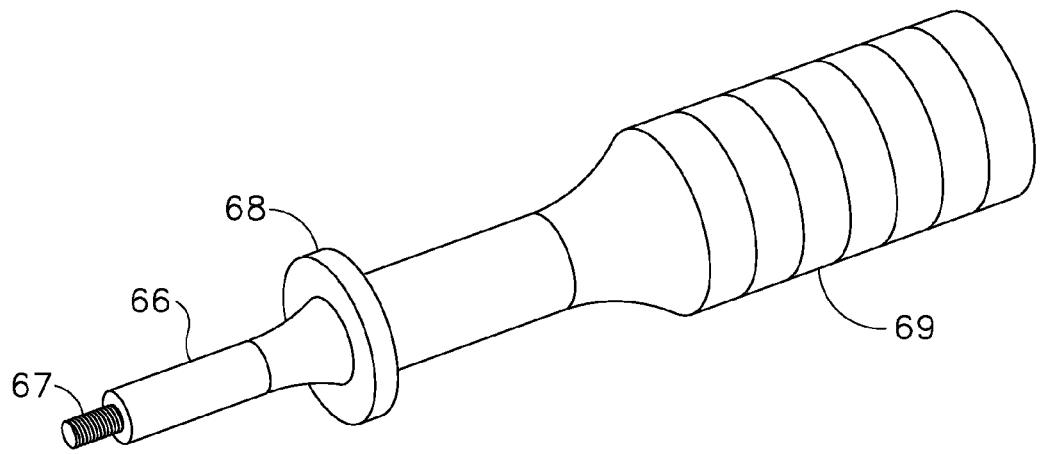
FIG. 6 depicts a perspective view of the transducer assembly of FIG. 5 with a transducer housing removed.

FIG. 6 depicts transducer assembly (12) with housing (60) removed. Mounting flange (68) near the distal end of transducer assembly (12) and piezoelectric stack (69) at the proximal end of transducer assembly (12) can be seen with housing (60) removed. When transducer assembly (12) of the present example is activated via a button (26), an electric field is created in piezoelectric stack (69), causing piezoelectric stack (69) and horn (66) to oscillate within and relative to housing (60). Mounting flange (68) is used to couple horn (66) to housing (60), to thereby support piezoelectric stack (69) in housing (60). Mounting flange (68) is located at a node associated with resonant ultrasonic vibrations communicated through piezoelectric stack (69) and horn (66). Transducer assembly (12) is operable to create mechanical energy, or vibrations, at an ultrasonic frequency (such as 55.5 kHz). If transducer assembly (12) is coupled to waveguide (102) via horn (66), then these mechanical oscillations are transmitted through waveguide (102) to ultrasonic blade (100) of end effector (40). In the present example, ultrasonic blade (100), being coupled to waveguide (102), oscillates at the ultrasonic frequency. Thus, when tissue is secured between ultrasonic blade (100) and clamp arm (44), the ultrasonic oscillation of ultrasonic blade (100) may sever and/or seal the tissue. While some exemplary features and configurations for transducer assembly (12) have been described, still other suitable features and configurations for transducer assembly (12) will be apparent to one of ordinary skill in the art in view of the teachings herein.

Ultrasonic vibrations that are generated by transducer assembly (12) are communicated along an acoustic waveguide (102), which extends through shaft assembly (30) to reach ultrasonic blade (100), as shown in FIGS. 2A-2B. As shown in FIG. 4, waveguide (102) is secured within shaft assembly (30) via a pin (33), which passes through waveguide (102) and shaft assembly (30). Pin (33) is located at a position along the length of waveguide (102) corresponding to a node associated with resonant ultrasonic vibrations communicated through waveguide (102). As noted above, when ultrasonic blade (100) is in an activated state (i.e., vibrating ultrasonically), ultrasonic blade (100) is operable to effectively cut through and seal tissue, particularly when the tissue is being compressed between clamp arm (44) and ultrasonic blade (100). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of ultrasonic blade (100) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (12) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (102) to reach ultrasonic blade (100), thereby providing oscillation of ultrasonic blade (100) at the resonant ultrasonic frequency. Thus, when tissue is secured between ultrasonic blade (100) and clamp pad (58), the ultrasonic oscillation of ultrasonic blade (100) may simultaneously sever the tissue and denature the proteins in adjacent tissue cells, thereby providing a coagulative effect with relatively little thermal spread. In some versions, an electrical current may also be provided through one or both of ultrasonic blade (100) or clamp pad (58) to electrocauterize the tissue. For instance, monopolar or bipolar RF energy may be provided through one or both of ultrasonic blade (100) or clamp pad (58). While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively activate transducer assembly (12) to thereby activate ultrasonic blade (100). In the present example, two buttons (26) are provided—one for activating ultrasonic blade (100) at a low power and another for activating ultrasonic blade (100) at a high power. However, it should be understood that any other suitable number of buttons and/or otherwise selectable power levels may be provided. Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions. It should also be understood that various other kinds of user input features may be used to selectively activate transducer assembly (12). For instance, a foot pedal may be provided to selectively activate transducer assembly (12).

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940; U.S. Pub. No. 2011/0015660; U.S. Pub. No. 2012/0112687; U.S. Pub. No. 2012/0116265; U.S. patent application Ser. No. 13/538,588; and/or U.S. patent application Ser. No. 13/657,553. Additional merely illustrative variations for instrument (10) will be described in greater detail below. It should be understood that the below described variations may be readily applied to instrument (10) described above and any of the instruments referred to in any of the references that are cited herein, among others.

II. Exemplary Clamp Pad Retention Variations

In some instances, clamp pad (58) may be undesirably removed from clamp arm (44). For instance, a user may improperly attempt to remove a clamp pad (58) from clamp arm (44). It may therefore be desirable to make it more difficult to remove clamp pad (58) from clamp arm (44). In addition or in the alternative, there may be other reasons to change the relationship between clamp pad (58) and clamp arm (44), such that clamp pad (58) is secured to clamp arm (44) in a manner different from that described above. Various exemplary alternative relationships between clamp pad (58) and clamp arm (44) will be described in greater detail below, while still other exemplary alternative relationships will be apparent to those of ordinary skill in the art in view of the teachings herein. It should be understood that the below examples may be readily incorporated into instrument (10), such that various teachings below may be readily combined with various teachings above as will be apparent to those of ordinary skill in the art.

A. Exemplary Clamp Arm with an Overmolded Clamp Pad

Figure 7:
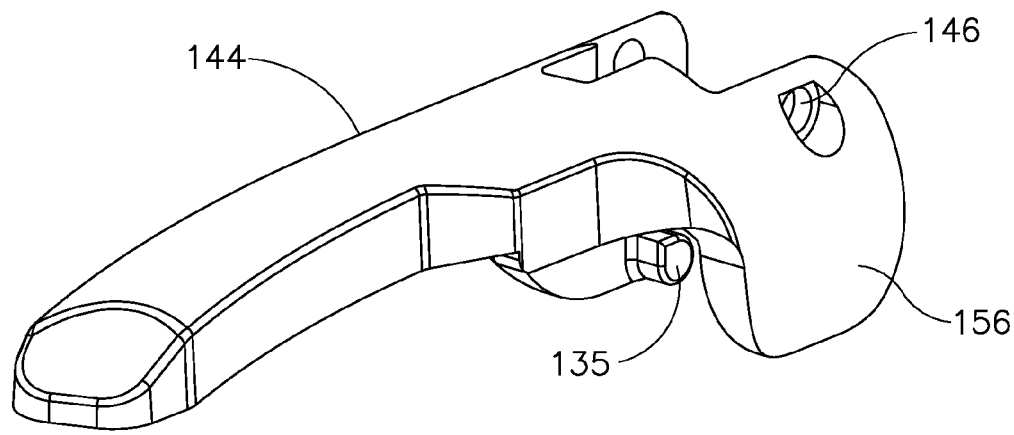
FIG. 7 depicts a perspective view of an exemplary alternative clamp arm suitable for incorporation with the instrument of FIG. 1.
Figure 9:
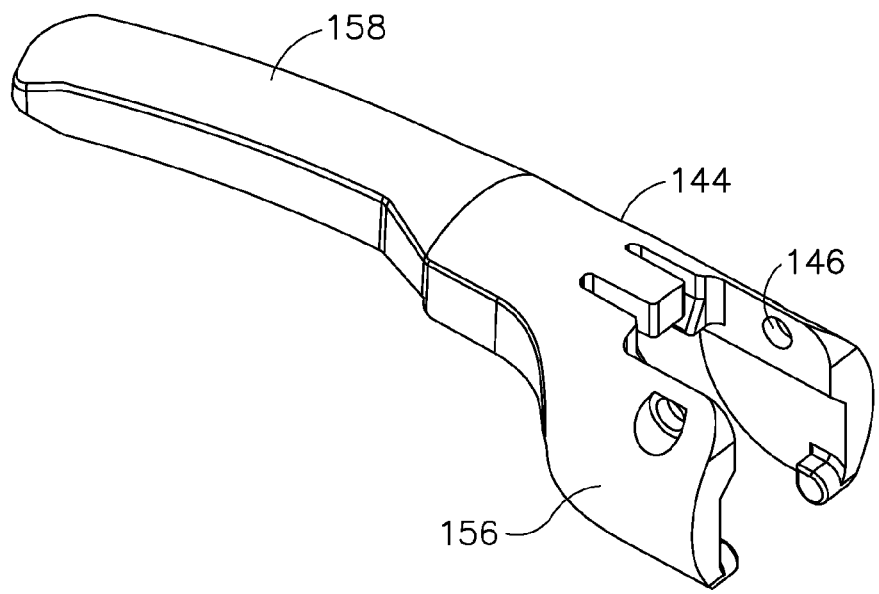
FIG. 9 depicts a perspective view of the clamp arm of FIG. 7 assembled with an overmolded clamp pad.
Figure 10:
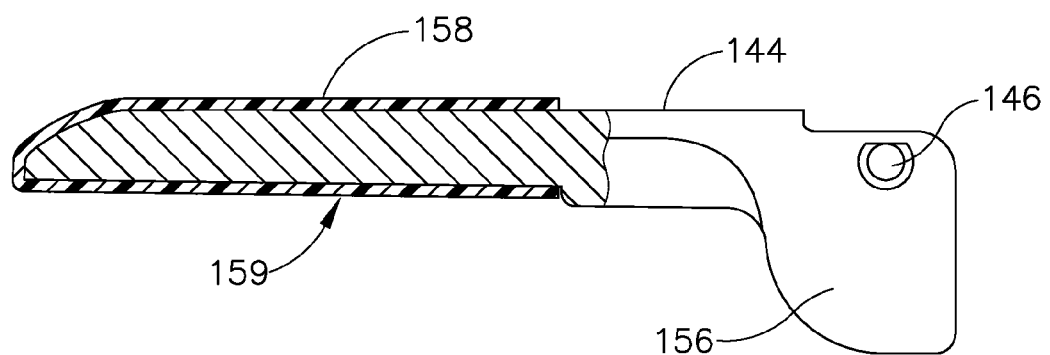
FIG. 10 depicts a cross sectional view of the assembled clamp arm and clamp pad of FIG. 9.

FIG. 7 shows an exemplary clamp arm (144) that is similar to clamp arm (44), except that clamp arm (144) does not include slots (53a, 55a) to receive a clamp pad (58). Instead, a clamp pad (158) is secured to clamp arm (144) via an overmold technique (FIGS. 9-10). Clamp arm (144) of the present example includes a pair of mounting extensions (156). Each extension (156) has a respective pin (135) and pin opening (146). Clamp arm (144) of the present example is formed of aluminum. However, any other suitable material or combination of materials may be used to form clamp arm (144).

Figure 8:
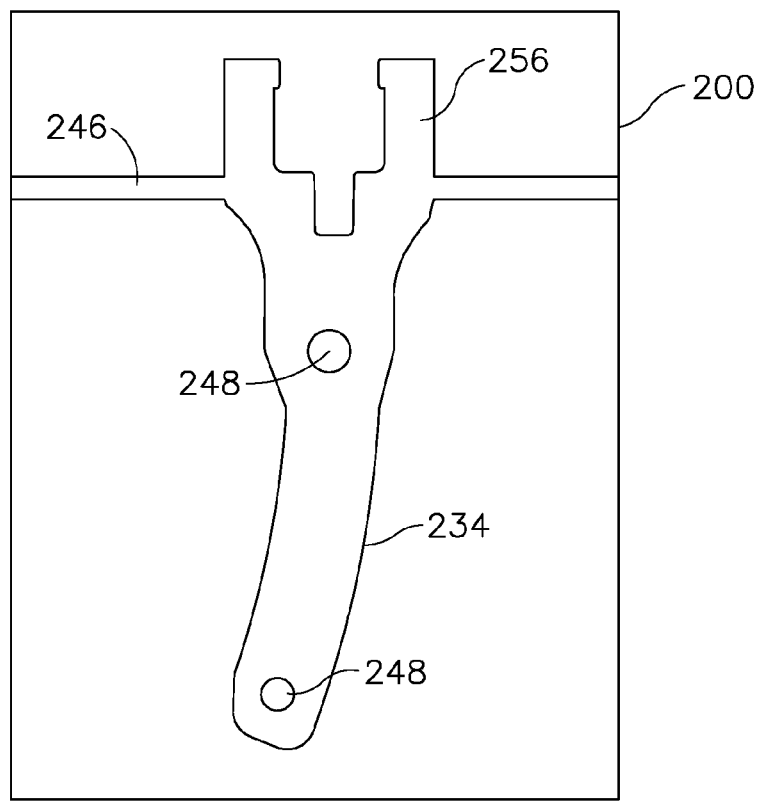
FIG. 8 depicts a cross sectional view of an exemplary mold device for use with the clamp arm of FIG. 7.

FIG. 8 shows an exemplary mold (200) that may be used to secure clamp pad (158) with clamp arm (144) by forming clamp pad (158) on clamp arm (144). Mold (200) includes a recess (234), a pair of stand-off posts (248), and a channel (246). Recess (234) is shaped to complement clamp arm (144) yet is sized larger than clamp arm (144). Stand-off posts (248) are configured to support clamp arm (144) within recess (234) and provide a gap between the surface of recess (234) and the outer surface of clamp arm (144). Clamp arm (144) is then placed within recess (234) such that extensions (156) on the proximal portion of clamp arm (144) are positioned within extensions (256) on the proximal portion of mold (200). Extensions (256) of mold (200) may be sized to engage extensions (156) of clamp arm (144) to thereby hold clamp arm (144) in place relative to mold (200). Clamp arm (144) may then be enclosed within mold (200). For example, another metal plate having any suitable configuration may be placed over mold (200) to enclose clamp arm (144) within mold (200). Other suitable methods of enclosing clamp arm (144) in mold (200) will be apparent to one with ordinary skill in the art in view of the teachings herein.

Channel (246) extends transversely across a proximal portion of recess (234). Channel (246) may be in fluid communication with a sprue feed. A coating material, such as polytetrafluoroethylene (PTFE) and/or other material(s), may then be introduced into mold (200) through channel (246). The introduced coating material fills recess (234) to thereby coat the distal portion of clamp arm (144) to form clamp pad (158), as shown in FIGS. 9-10. As the coating material fills recess (234) proximally, the coating material then runs through the opposite channel (246) and out of mold (200). When the coating material runs out of the exit channel (246), extensions (156) of clamp arm (144) may remain uncoated. Accordingly, clamp pad (158) is secured to clamp arm (144) by mechanical and thermal bonding through a one-shot coating process. As shown in FIGS. 9-10, clamp pad (158) is molded onto clamp arm (144) to encompass the entire distal portion of clamp arm (144). In other versions, clamp pad (158) may cover selected portions of clamp arm (144), such as the distal portion of clamp arm (144) that is adjacent to blade (100). Other selected coating areas will be apparent to one with ordinary skill in the art in view of the teachings herein. It should also be understood that various kinds of surface features may be formed in the tissue contacting region (159) of clamp pad (158) through the molding process. Several merely illustrative examples of such surface features are described in greater detail below, while other examples will be apparent to those of ordinary skill in the art in view of the teachings herein.

When clamp arm (144) is removed from mold (200), clamp arm (144) with overmolded clamp pad (158) may then be coupled with inner tube (34) of shaft assembly (30) via integral pins (135) of clamp arm (144). Clamp arm (144) with overmolded clamp pad (158) may also be coupled with outer sheath (32) of shaft assembly (30) by placing a pin (45) through openings (146) on clamp arm (144).

Figure 11:
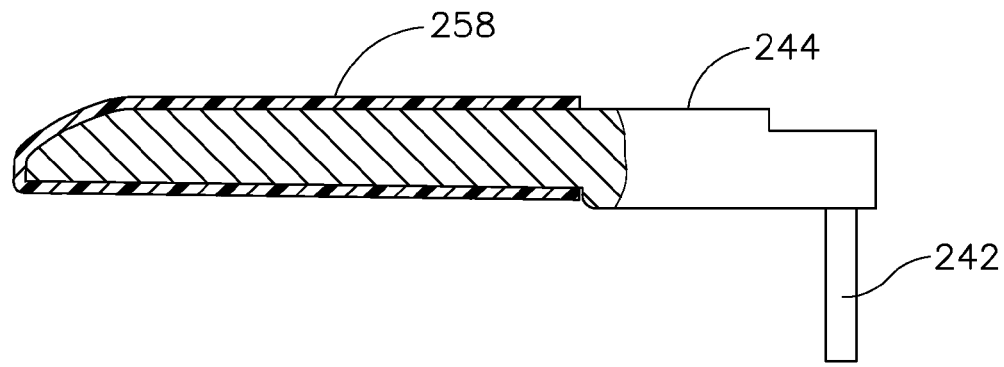
FIG. 11 depicts a cross sectional view of an exemplary alternative overmolded clamp arm assembly suitable for incorporation with the instrument of FIG. 1.
Figure 12:
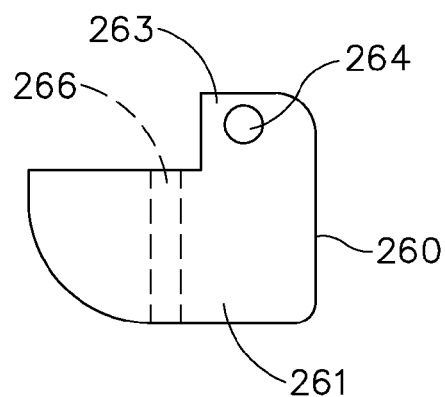
FIG. 12 depicts a side elevational view of a mounting device for use with a clamp arm of FIG. 11.
Figure 13:
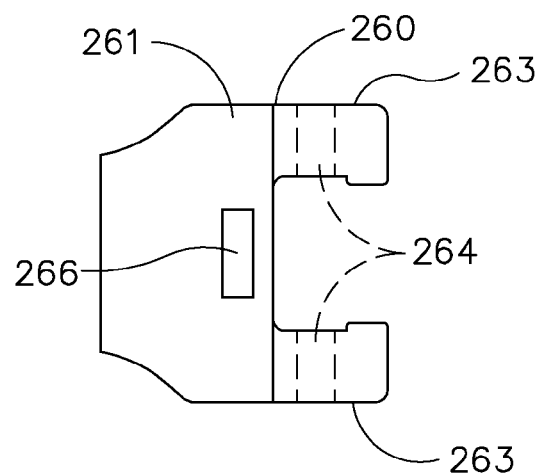
FIG. 13 depicts a top view of the mounting device of FIG. 12.

In some versions, clamp arm (144) is coupled with inner tube (34) via an additional coupling device (260). FIG. 11 shows another exemplary clamp arm (244) that is similar to clamp arm (144) in that clamp arm (244) comprises an overmolded clamp pad (258). However, clamp arm (244) of this example comprises a proximal extension (242) that is configured to be inserted within coupling device (260). In the present example, clamp pad (258) is molded distal to extension (242). As shown in FIGS. 12-13, coupling device (260) comprises a distal portion (261) and a pair of proximal extensions (263). Distal portion (261) defines an opening (266) that is configured to receive extension (242) of clamp arm (242). Proximal extensions (263) define openings (264) that are used to assemble coupling device (260) with inner tube (34) of instrument (10).

Figure 14:
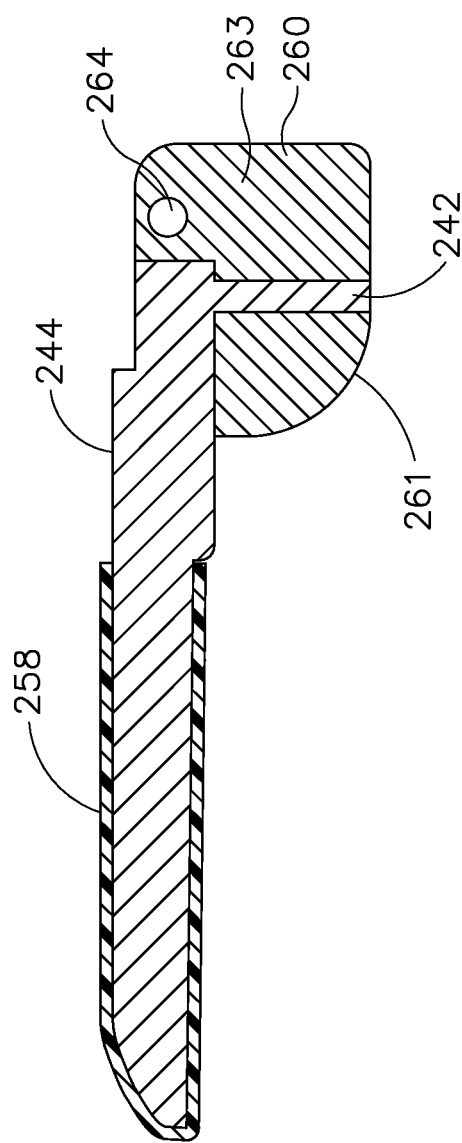
FIG. 14 depicts a cross sectional view of the overmolded clamp arm assembly of FIG. 11 assembled with the mounting device of FIG. 12.

FIG. 14 shows clamp arm (244) assembled with coupling device (260). Extension (242) of clamp arm (244) is inserted within opening (266) of coupling device (260). Opening (266) may be sized to provide a friction fit with clamp arm (244) to secure clamp arm (244) in place relative to coupling device (260). Coupling device (260) may further include a resilient member (not shown) that is resiliently biased to engage extension (242) of clamp arm (244) when extension (242) is inserted within coupling device (260). Accordingly, an assist tool may be used to insert and/or remove clamp arm (244) with coupling device (260). Other suitable methods of securing clamp arm (244) within coupling device (260) will be apparent to one with ordinary skill in the art in view of the teachings herein. As shown in FIG. 14, the proximal end of clamp arm (244) engages extensions (263) of coupling device (260). Coupling device (260) may include integral inwardly directed pins, similar to pins (35), to pivotally secure coupling device (260) to inner tube (34). Extensions (263) may be coupled with outer sheath (32) of instrument (10) by placing pin (45) through openings (264) of coupling device (260). Coupling device (260) may therefore allow repeated clamping by clamp arm (244). In some versions, clamp arm (244) and overmolded clamp pad (258) may be removed from coupling device (260) without removing coupling device (260) from instrument (10) to separately dispose of clamp arm (244) and clamp pad (258) after use. Other coupling configurations will be apparent to one with ordinary skill in the art in view of the teachings herein.

B. Exemplary Clamp Arm Retention Tabs

Figure 15:
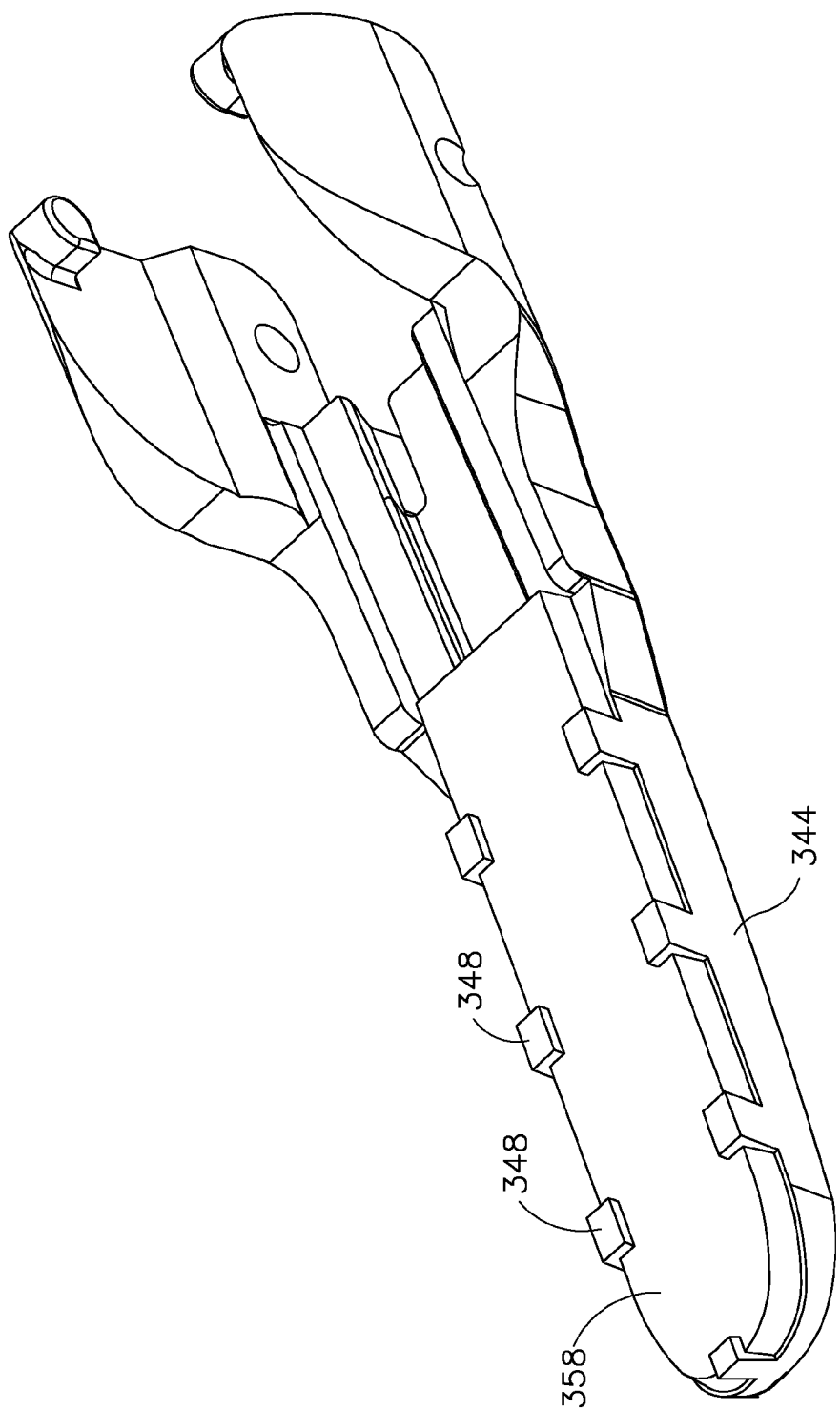
FIG. 15 depicts a partial perspective view of an exemplary alternative clamp arm assembly with tabs suitable for incorporation with the instrument of FIG. 1.

FIG. 15 shows a clamp arm (344) that is similar to clamp arm (44), except that clamp arm (344) comprises a plurality of inwardly directed tabs (348). Tabs (348) extend upwardly from clamp arm (344) and inwardly toward each other. Before tabs (348) are bent inwardly toward each other, a clamp pad (358), which is similar to clamp pad (58), may be inserted within clamp arm (344). Tabs (348) may then be bent inwardly toward each other to retain clamp pad (358) in clamp arm (344). Clamp arm (344) may then be coupled with inner tube (34) and outer sheath (32) as described above with respect to clamp arm (44). In addition to providing retention of clamp pad (358) in clamp arm (344), tabs (348) may further be used as grasping teeth to help grasp tissue between clamp arm (344) and ultrasonic blade (100).

In some versions, instrument (10) may be operable to seal tissue by applying RF energy to tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 7,354,440, entitled "Electrosurgical Instrument and Method of Use," issued Apr. 8, 2008, the disclosure of which is incorporated by reference herein. RF energy delivery capabilities of instrument (10) may be provided in accordance with at least some of the teachings of the above-cited reference. In versions of instrument (10) that include RF energy delivery capabilities, tabs (348) may further be used as RF electrodes. By way of example only, each tab (348) may be used as a discrete active electrode for monopolar RF electrocautery. As another merely illustrative example, tabs (348) may be used in pairs of provide bipolar RF electrocautery. Other suitable configurations and operabilities for tabs (348) will be apparent to one with ordinary skill in the art in view of the teachings herein.

C. Exemplary Clamp Pad Carrier

Figure 16:
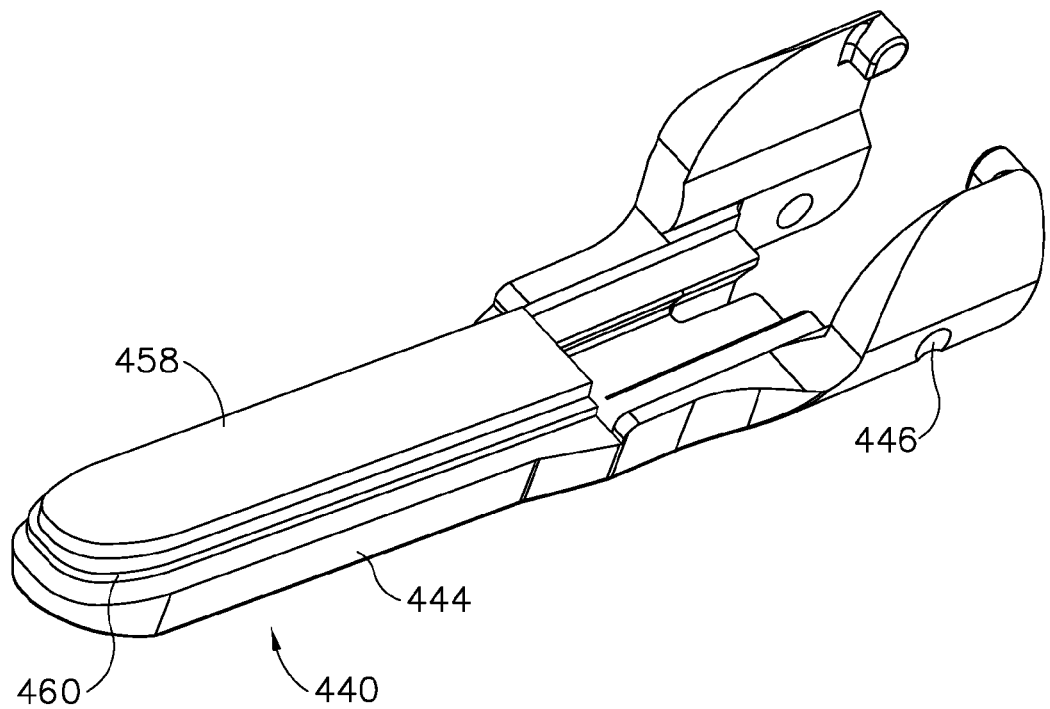
FIG. 16 depicts a bottom perspective view of an exemplary alternative clamp arm assembly suitable for incorporation with the instrument of FIG. 1.
Figure 17:
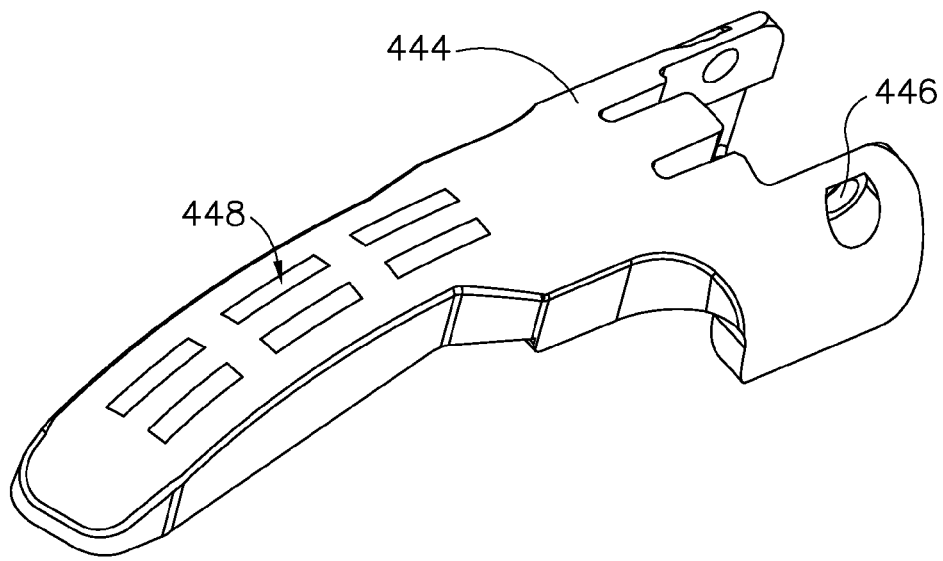
FIG. 17 depicts a top perspective view of a clamp arm of the clamp arm assembly of FIG. 16.
Figure 18:
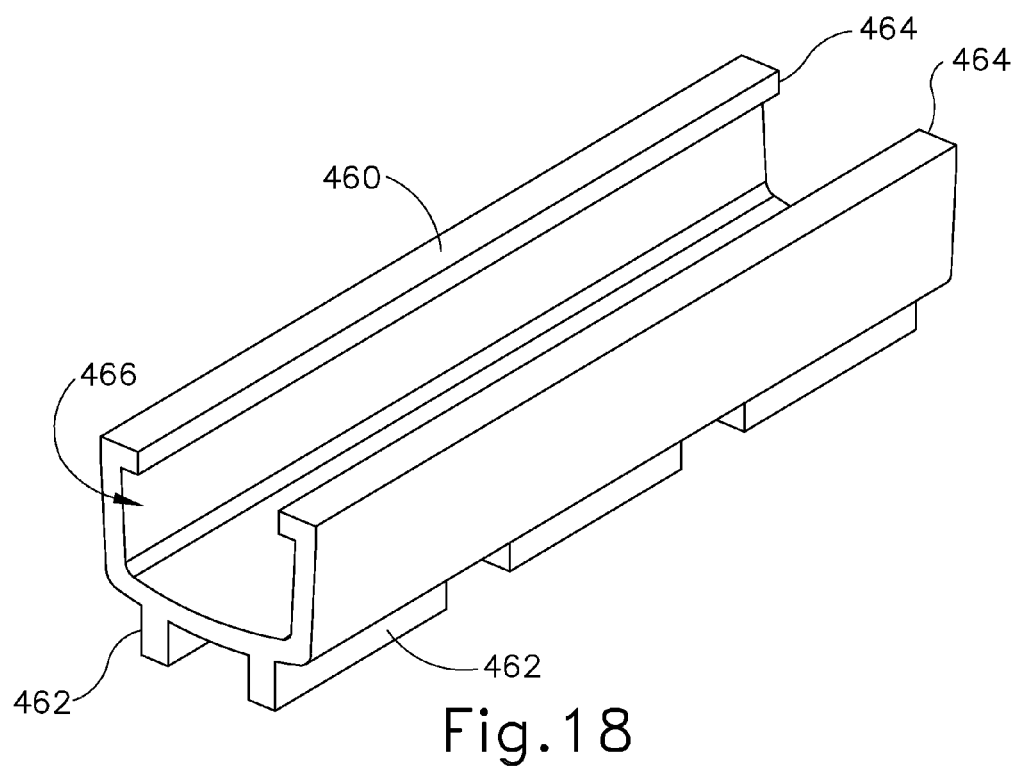
FIG. 18 depicts a top perspective view of a carrier of the clamp arm assembly of FIG. 16.
Figure 19:
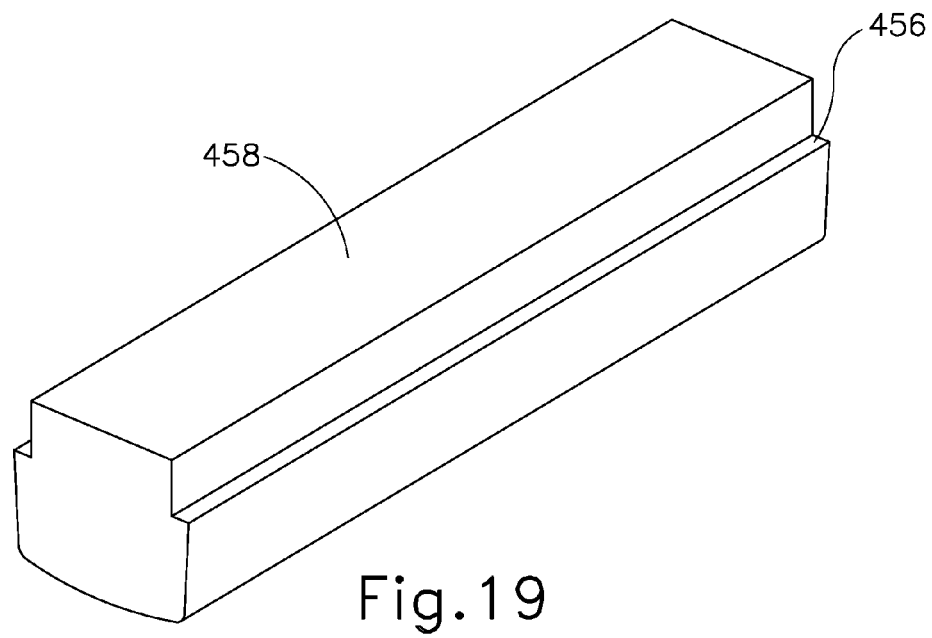
FIG. 19 depicts a top perspective view of a clamp pad of the clamp arm assembly of FIG. 16.

FIG. 16 shows an exemplary clamp arm assembly (440) that includes a clamp arm (444), a carrier (460), and a clamp pad (458). As shown in FIG. 17, clamp arm (444) is similar to clamp arm (44), except that clamp arm (444) comprises a plurality of slots (448) extending through the distal portion of clamp arm (444). FIG. 18 shows a carrier (460) comprising extensions (462), retention walls (464), and a channel (466). The plurality of extensions (464) extend outwardly from carrier (460) and are configured to be inserted within slots (448) of clamp arm (444). Walls (464) of carrier (460) extend inwardly to form channel (466), which extends longitudinally through carrier (460). Clamp pad (458) is configured to be inserted within channel (466) of carrier (460). As best seen in FIG. 19, clamp pad (458) comprises a ledge (456) on each side of clamp pad (458) complements and engages a corresponding wall (464) of carrier (460).

Figure 20:
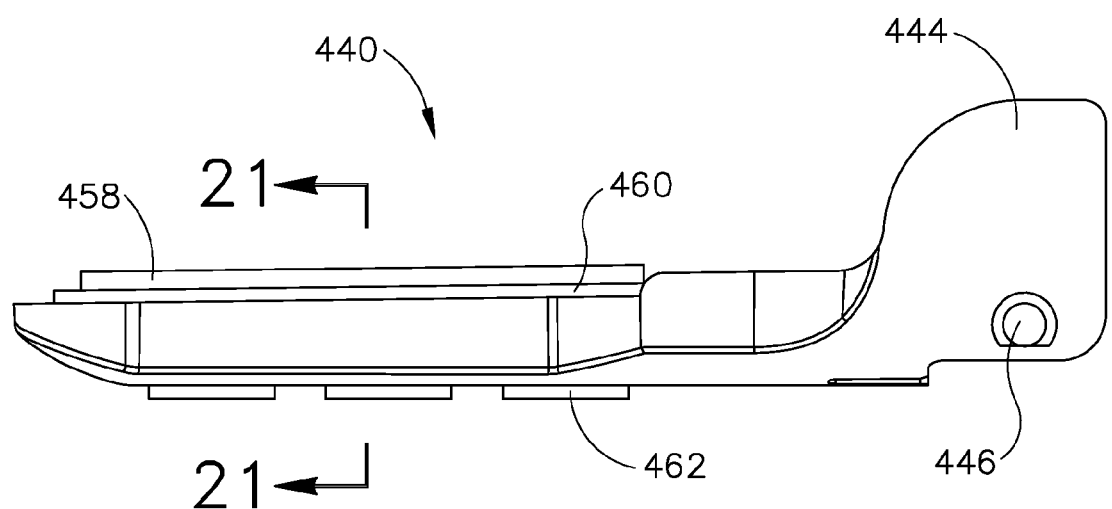
FIG. 20 depicts a side elevational view of the clamp arm assembly of FIG. 16.
Figure 21:
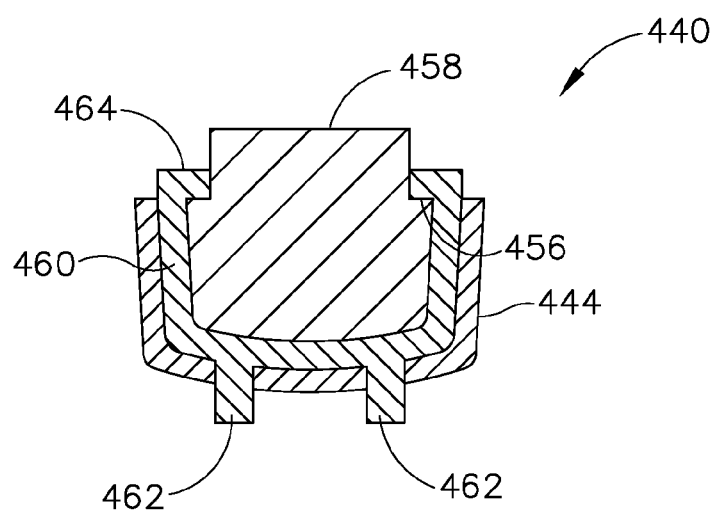
FIG. 21 depicts a cross sectional view of the clamp arm assembly of FIG. 16 taken along line 21-21 of FIG. 20.

To form clamp arm assembly (440) as shown in FIGS. 20-21, clamp pad (458) is inserted within channel (466) of carrier (460). Walls (464) of carrier (464) engage ledges (456) of clamp pad (458) to maintain clamp pad (458) within carrier (460). A portion of clamp pad (458) extends beyond carrier (460), past walls (464), to engage ultrasonic blade (100) or tissue against ultrasonic blade (100). With clamp pad (458) inserted in carrier (460), carrier (460) is then inserted within clamp arm (444) such that extensions (462) of carrier (460) are positioned within slots (448) of clamp arm (444). In the present example, extensions (462) extend beyond the outer surface clamp arm (444). The exposed portions of extensions (462) are further be secured to clamp arm (444) using an adhesive, heat staking, ultrasonic staking, and/or any other suitable technique as will be apparent to one with ordinary skill in the art in view of the teachings herein. Extensions (462) thereby secure carrier (460) relative to clamp arm (444). In some other versions, extensions (462) are embedded within clamp arm (444). Once carrier (460) is secured to clamp arm (444), clamp arm assembly (440) may then be coupled with outer tube (32) of shaft assembly (30) by placing pin (45) through openings (446) on clamp arm (444). Clamp arm (444) may include integral inwardly directed pins, similar to pins (35), to pivotally secure clamp arm (444) to inner tube (34). Other coupling configurations will be apparent to one with ordinary skill in the art in view of the teachings herein.

D. Exemplary Clamp Arm with Barbs

Figure 22:
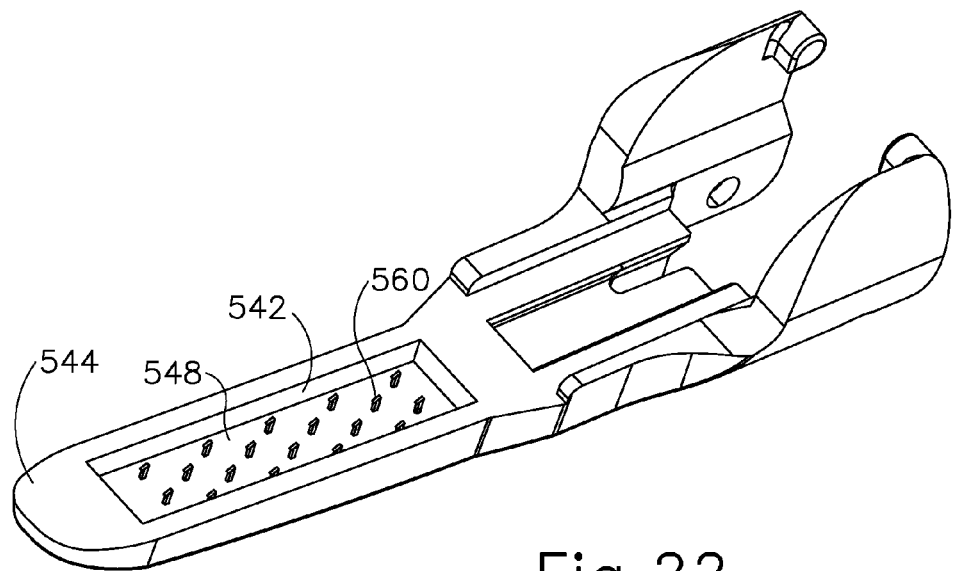
FIG. 22 depicts a partial perspective view of an exemplary alternative clamp arm with barbs suitable for incorporation with the instrument of FIG. 1.
Figure 23:
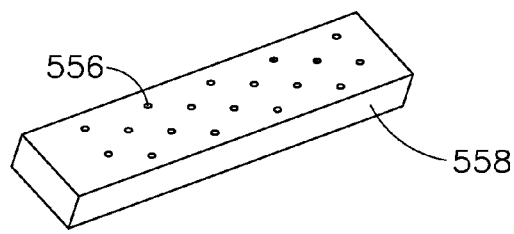
FIG. 23 depicts a perspective view of a clamp pad for use with the clamp arm of FIG. 22.
Figure 24:
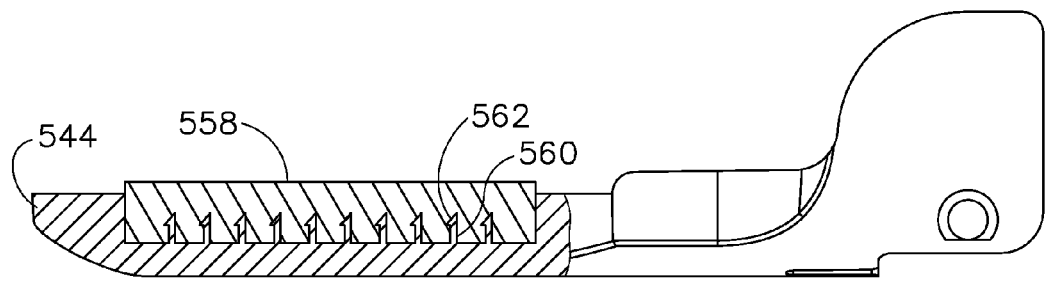
FIG. 24 depicts a cross sectional view of the clamp pad of FIG. 23 assembled with the clamp arm of FIG. 22.

FIG. 22 shows another exemplary clamp arm (544) that is similar to clamp arm (44), except that clamp arm (544) of this example comprises a plurality of barbs (560) extending outwardly from an inner wall (548) of clamp arm (544). Although barbs (560) are shown in FIG. 22 as extending from a bottom surface of clamp arm (544), barbs (560) may extend from any inner surface of clamp arm (544). Barbs (560) may be formed on inner wall (548) of clamp arm (544) through any suitable process, such as machining, forming, molding, growing, a MEMS process, etc. As best seen in FIG. 24, each barb (560) comprises a protrusion (562) that projects outwardly from barb (560). Barbs (560) may therefore engage clamp pad (558) to secure clamp pad (558) relative to clamp arm (544). FIG. 23 shows a version of clamp pad (558) that defines a plurality of openings (556) that correspond to barbs (560). Accordingly, clamp pad (558) is inserted within clamp arm (544) such that barbs (560) are positioned within openings (556) of clamp pad (558), as shown in FIG. 24.

In some versions, openings (556) are omitted from clamp pad (558) such that barbs (560) are driven through and into an exterior surface of clamp pad (558). Clamp pad (558) may be pressed onto barbs (560) without preheating clamp pad (558). Alternatively, clamp pad (558) and/or clamp arm (544) may be preheated to assist in forming of clamp pad (558) around barbs (560). In some variations, barbs (560) are replaced with T-shaped nanonails. Other suitable configurations for barbs (560) will be apparent to one with ordinary skill in the art in view of the teachings herein. Once clamp pad (558) is secured to clamp arm (544), clamp arm (544) may then be coupled with outer tube (32) of shaft assembly (30) by placing pin (45) through openings (546) on clamp arm (544). Clamp arm (544) may include integral inwardly directed pins, similar to pins (35), to pivotally secure clamp arm (544) to inner tube (34). Other coupling configurations will be apparent to one with ordinary skill in the art in view of the teachings herein.

E. Exemplary Laterally Grooved Clamp Arm

Figure 25:
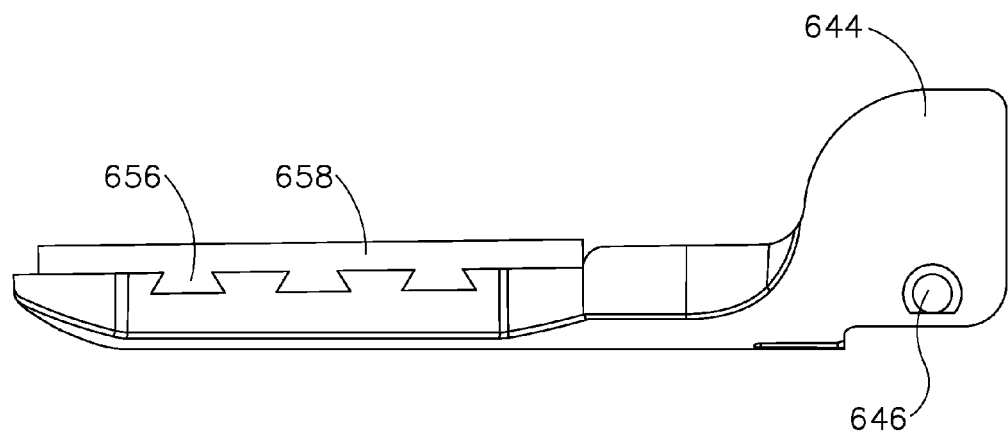
FIG. 25 depicts a cross sectional view of an exemplary alternative clamp arm assembly with grooves suitable for incorporation with the instrument of FIG. 1.
Figure 26:
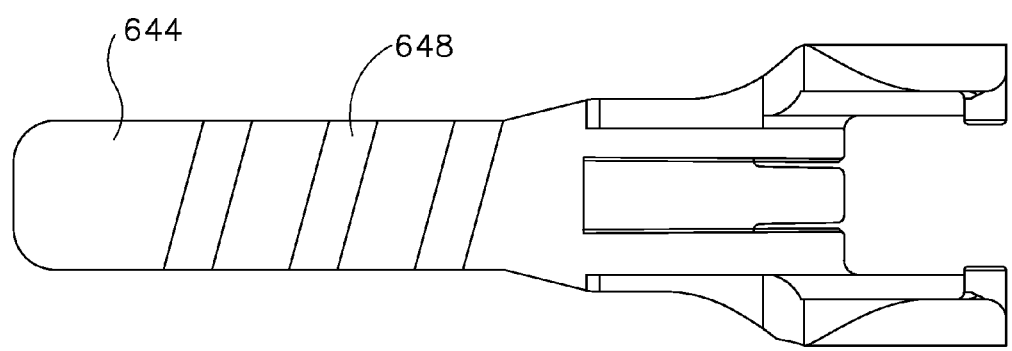
FIG. 26 depicts a bottom plan view of a clamp arm of the clamp arm assembly of FIG. 25.

FIGS. 25-26 show another exemplary clamp arm (644) that is similar to clamp arm (44), except that clamp arm (644) of this example comprises a plurality of grooves (648) extending laterally across clamp arm (644). As best seen in FIG. 26, grooves (648) extend at an oblique angle across clamp arm (644) to lengthen the retention area. While grooves (648) extend at oblique angles relative to the longitudinal axis of clamp arm (644) in this example, grooves (648) extend along paths that are parallel to each other. In some other versions, grooves (648) extend across clamp arm (644) along respective paths that are perpendicular to the longitudinal axis of clamp arm (644). Grooves (648) are configured to receive complementary protrusions (656) of clamp pad (658). Clamp pad (658) is similar to clamp pad (58), except that protrusions (656) extend outwardly from clamp pad (658) along paths that are oblique to the longitudinal axis of clamp pad (658). In the present example, protrusions (656) and grooves (648) have a dovetailed configuration to retain protrusions (656) within grooves (648). Of course, other suitable configurations will be apparent to one with ordinary skill in the art in view of the teachings herein. Accordingly, clamp pad (658) is inserted within clamp arm (644) such that grooves (648) of clamp arm (644) receive protrusions (656) of clamp pad (658) to thereby retain clamp pad (658) relative to clamp arm (644), as shown in FIG. 25.

Once clamp pad (658) is secured to clamp arm (644), clamp arm (644) may then be coupled with outer tube (32) of shaft assembly (30) by placing pin (45) through openings (646) on clamp arm (644). Clamp arm (644) may include integral inwardly directed pins, similar to pins (35), to pivotally secure clamp arm (644) to inner tube (34). Other coupling configurations will be apparent to one with ordinary skill in the art in view of the teachings herein.

F. Exemplary Clamp Arm with T-Slot

Figure 27A:
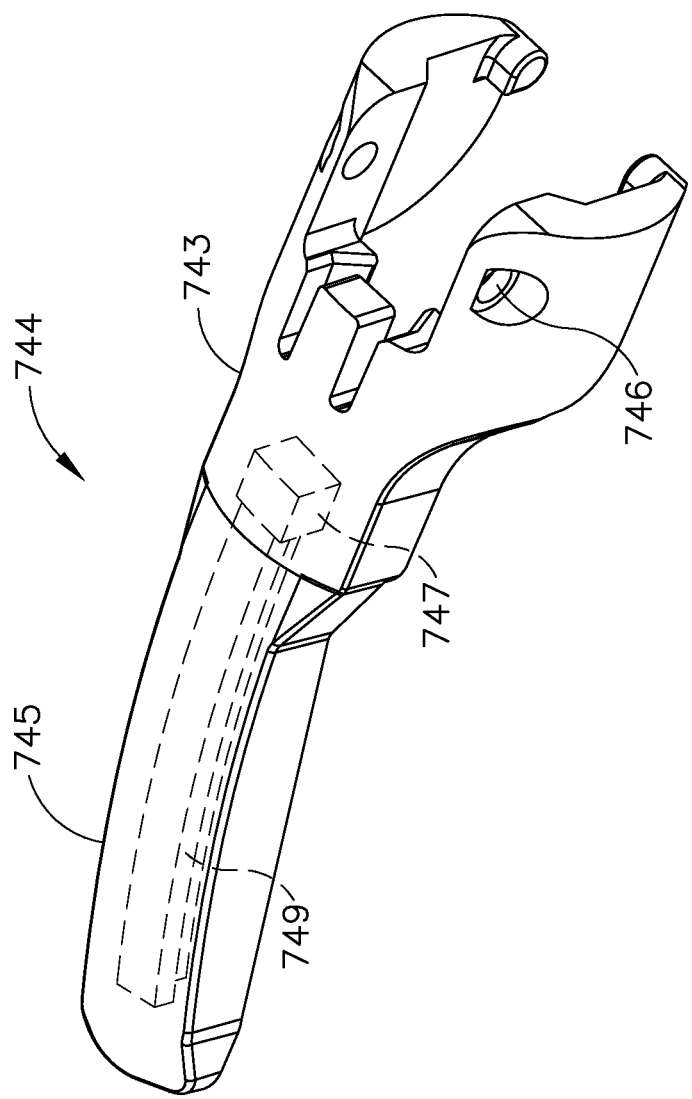
FIG. 27A depicts a top perspective view of an exemplary alternative clamp arm with a t-slot configuration suitable for incorporation with the instrument of FIG. 1.
Figure 27B:
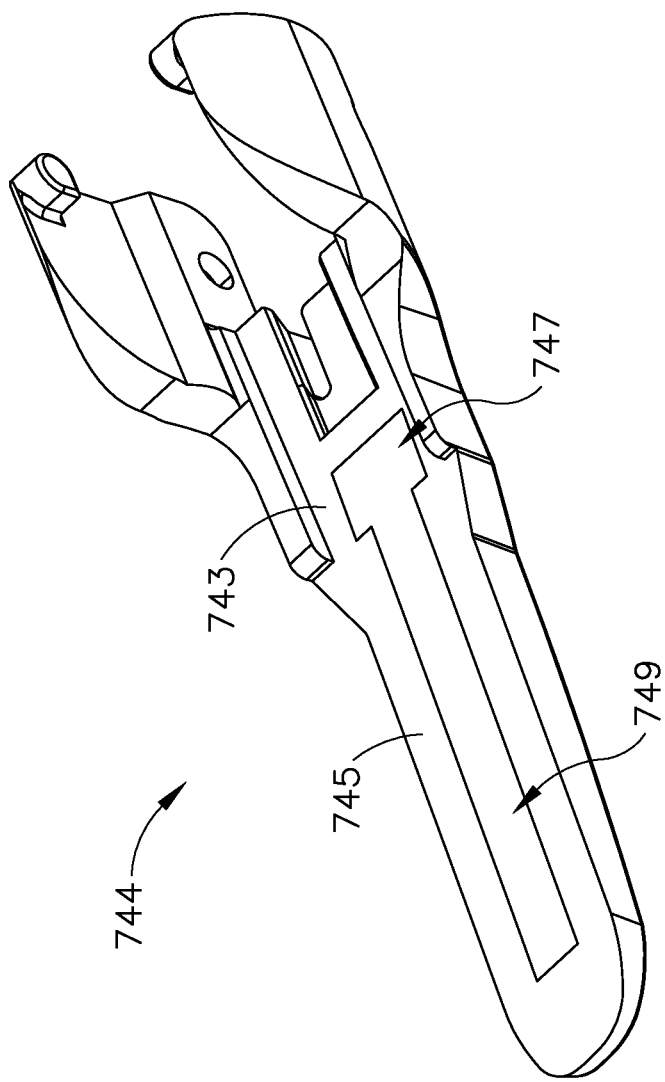
FIG. 27B depicts a bottom perspective view of the clamp arm of FIG. 27A.

FIGS. 27A-27B show another exemplary clamp arm (744) for use with instrument (10). Clamp arm (744) is similar to clamp arm (44) in that clamp arm (744) includes a distal T-shaped slot (749) and a proximal wedged-shaped or dovetail-shaped slot (747). T-shaped slot (749) is similar to T-shaped slot (53a) of clamp arm (44) and wedged-shaped slot (747) is similar to wedged-shaped slot (55a) of clamp arm (44). However, as shown in FIG. 27A, T-shaped slot (749) of clamp arm (744) extends distally longer than T-shaped slot (53a) of clamp arm (44). Accordingly, wedged-shaped slot (747) of the present example is shorter than wedged-shaped slot (55a) of clamp arm (44). This may help retain a clamp pad (58) within clamp arm (744). As shown in FIG. 27B, clamp arm (744) comprises a distal portion (745) with T-shaped slot (749) and a proximal portion (743) with wedged-shaped slot (747). This may allow for machinability of clamp arm (744) such that distal portion (745) is assembled with proximal portion (743) after the pieces are machined. Of course, clamp arm (744) may be formed from one integral piece. Other suitable slot (747, 749) configurations will be apparent to one with ordinary skill in the art in view of the teachings herein.

Once a clamp pad (58) is secured to clamp arm (744), clamp arm (744) may then be coupled with outer tube (32) of shaft assembly (30) by placing pin (45) through openings (746) on clamp arm (744). Clamp arm (744) may include integral inwardly directed pins, similar to pins (35), to pivotally secure clamp arm (744) to inner tube (34). Other coupling configurations will be apparent to one with ordinary skill in the art in view of the teachings herein.

G. Exemplary Clamp Arm with Sidewall Slots

Figure 28:
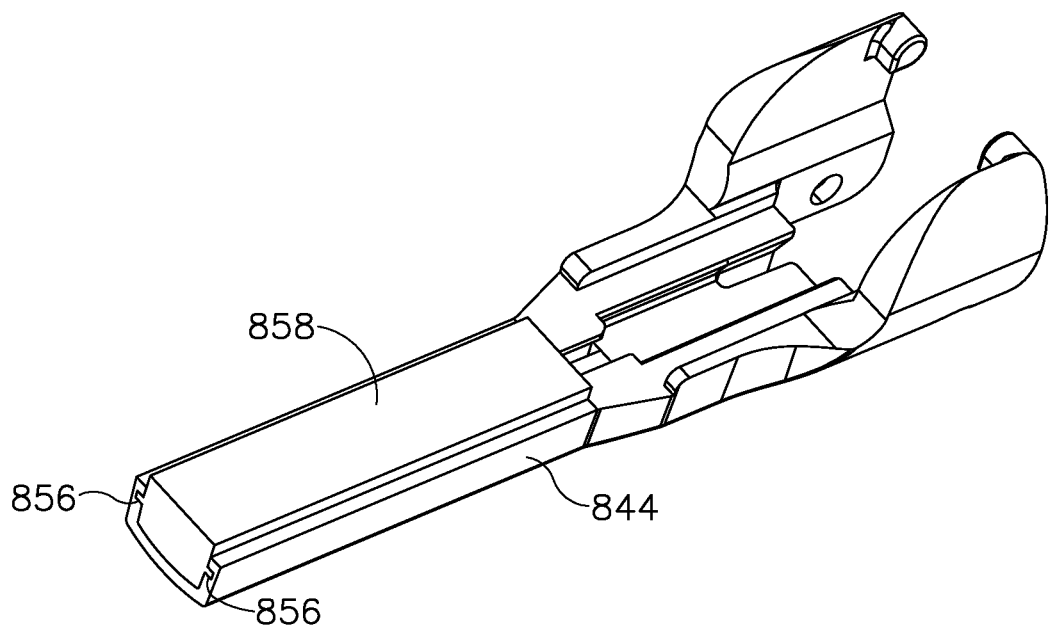
FIG. 28 depicts a partial perspective view of an exemplary alternative clamp arm assembly with sidewall slots suitable for incorporation with the instrument of FIG. 1.
Figure 29:
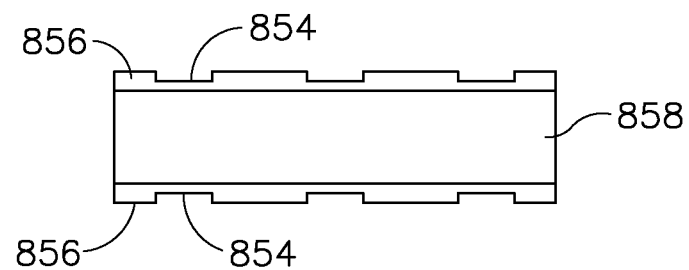
FIG. 29 depicts a top plan view of a clamp pad of the clamp arm assembly of FIG. 28.
Figure 30:
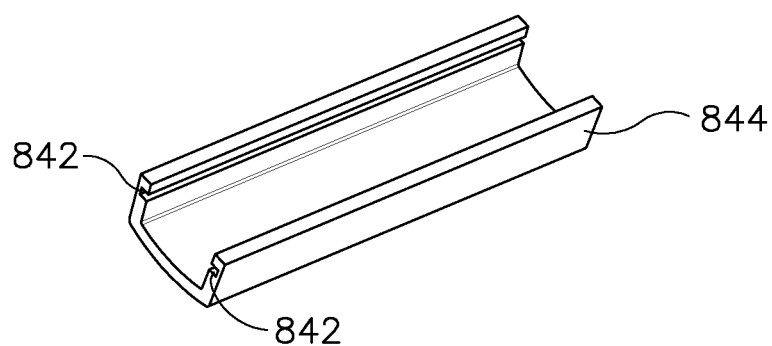
FIG. 30 depicts a partial perspective view of a clamp arm of the clamp arm assembly of FIG. 28.

FIGS. 28 and 30 show another exemplary clamp arm (844) that is similar to clamp arm (44), except that clamp arm (844) of this examples comprises side channels (842) extending longitudinally within clamp arm (844). Channels (842) are configured to receive protrusions (856) of a clamp pad (858). As best seen in FIG. 29, clamp pad (858) is similar to clamp pad (58), except that clamp pad (858) comprises a plurality of protrusions (856) extending outwardly from clamp pad (858) in the form of rails. Protrusions (856) are configured to be inserted within channels (842) of clamp arm (844) to thereby maintain clamp pad (858) within clamp arm (844), as shown in FIG. 28. In the present example, clamp pad (858) defines recesses (854) between protrusions (856) of clamp pad (858). Channels (842) of clamp arm (844) may include corresponding protrusions that insert within recesses (854) of clamp pad (858) to further secure clamp pad (858) with clamp arm (844). Other suitable channel (842) and protrusion (856) configurations will be apparent to one with ordinary skill in the art in view of the teachings herein.

Once clamp pad (858) is secured to clamp arm (844), clamp arm (844) may then be coupled with outer tube (32) of shaft assembly (30) by placing pin (45) through openings, similar to openings (46), on clamp arm (844). Clamp arm (844) may include integral inwardly directed pins, similar to pins (35), to pivotally secure clamp arm (844) to inner tube (34). Other coupling configurations will be apparent to one with ordinary skill in the art in view of the teachings herein.

H. Exemplary Clamp Arm Pin

Figure 31:
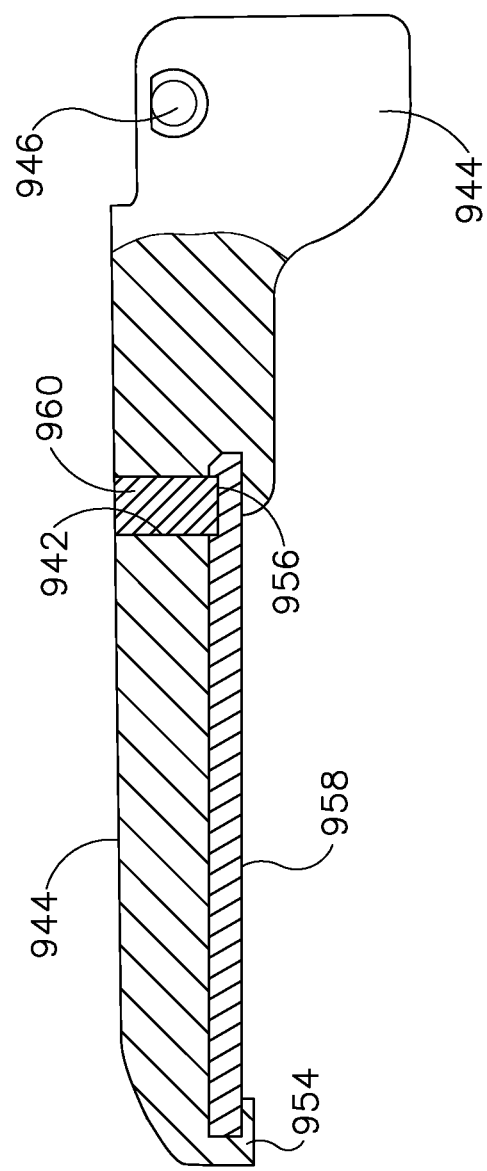
FIG. 31 depicts a partial cross sectional view of an exemplary alternative clamp arm assembly with a pin suitable for incorporation with the instrument of FIG. 1.

FIG. 31 shows a clamp arm (944) that is similar to clamp arm (44), except that clamp arm (944) defines a transverse opening (942) that is configured to receive a retention pin (960). In the present example, clamp arm (944) is coupled with clamp pad (958). Clamp pad (958) is similar to clamp pad (58), except that clamp pad (958) defines an indentation (956) that is configured to receive pin (960). Accordingly, clamp pad (958) is coupled with clamp arm (944) such that opening (942) of clamp arm (944) is aligned with indentation (956) of clamp pad (958). Pin (960) may then be inserted through opening (942) and into indentation (956), as shown in FIG. 31. Pin (960) may be held in place within opening (942) of clamp arm (944) by an interference fit with opening (942), or pin (960) may be welded in place, or pin (960) may be secured in clamp arm (944) in any other suitable fashion. Other suitable methods for securing pin (960) within opening (942) of clamp arm (944) will be apparent to one with ordinary skill in the art in view of the teachings herein. Pin (960) may interface with clamp pad (958) by pressing clamp pad (985) away from clamp arm (944), thereby driving a dovetail rail, T-shaped rail, or other kind of rail against inner surfaces of a complementary channel in clamp arm (944) to locking clamp pad (985) in place through friction. In addition or in the alternative, pin (960) may provide a positive stop proximal to clamp pad (958) such that pin (960) prevents clamp pad (985) from sliding proximally relative to clamp arm (944). A distal boss (954) of clamp arm (944) may prevent clamp pad (985) from sliding distally relative to clamp arm (944), such that clamp pad (985) is longitudinally captured between distal boss (954) and pin (960).

While indentation (956) only engages the distal portion of the bottom of pin (960) in the present example, indentation (956) may instead be formed as an opening to fully enclose pin (960) within clamp pad (958). This may further prevent clamp pad (958) from moving distally relative to clamp arm (944). Other suitable relationships between pin (960) and clamp pad (958) will be apparent to those of ordinary skill in the art in view of the teachings herein. Similarly, other suitable configurations for pin (960) and clamp pad (958) will be apparent to one with ordinary skill in the art in view of the teachings herein.

Once clamp pad (958) is secured to clamp arm (944), clamp arm (944) may then be coupled with outer tube (32) of shaft assembly (30) by placing pin (45) through openings (946) on clamp arm (944). Clamp arm (944) may include integral inwardly directed pins, similar to pins (35), to pivotally secure clamp arm (944) to inner tube (34). Other coupling configurations will be apparent to one with ordinary skill in the art in view of the teachings herein.

III. Exemplary Clamp Arm with Tissue Grasping Features

In some instances, it may be desirable to include grasping features on clamp pad (58), clamp arm (44), and/or blade (100) that facilitates the grasping of tissue between clamp pad (58) and blade (100). Such tissue grasping features may thereby improve sealing and/or cutting of the tissue between clamp pad (58) and blade (100). In addition or in the alternative, such grasping features may prevent migration of tissue between clamp pad (58) and blade (100) while blade (100) is ultrasonically activated. Several exemplary grasping features that may be incorporated into clamp pad (58) are discussed in greater detail below, while several other examples will be apparent to those of ordinary skill in the art in view of the teachings herein.

A. Exemplary Clamp Pad with Grooves

Figure 32:
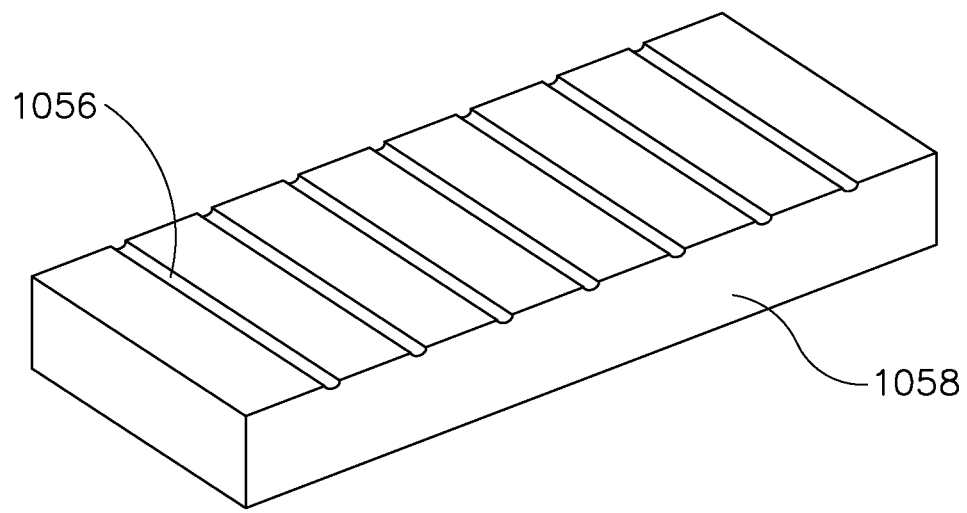
FIG. 32 depicts a perspective view of an exemplary alternative clamp pad with lateral grooves suitable for incorporation with the instrument of FIG. 1.
Figure 33:
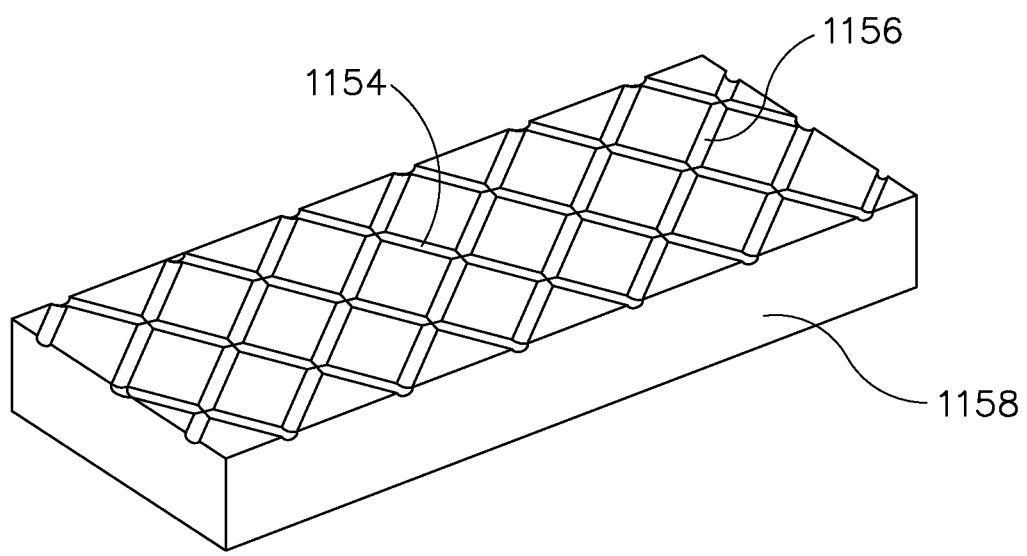
FIG. 33 depicts a perspective view of an exemplary alternative clamp pad with interwoven grooves suitable for incorporation with the instrument of FIG. 1.

FIG. 32 shows an exemplary alternative clamp pad (1058) that is similar to clamp pad (58), except that clamp pad (1058) of this example comprises a plurality of grooves (1056) extending across an exterior surface of clamp pad (1058). Grooves (1056) may be positioned adjacent to blade (100) (and/or tissue) when clamp pad (1058) is assembled within clamp arm (44) of instrument (10) such that grooves (1056) act to help grasp tissue between clamp pad (1058) and blade (100). In the present example, grooves (1056) extend transversely across clamp pad (1058), along paths that are perpendicular to the longitudinal axis of clam pad (1058). Alternatively, grooves (1056) may extend across clamp pad (1058) at varying angles. For example, FIG. 33 shows a clamp pad (1158) that is similar to clamp pad (1058), except that clamp pad (1158) includes grooves (1154, 1156) that extend obliquely across an exterior surface of clamp pad (1158). In particular, one set of parallel grooves (1154) is positioned at a first oblique angle and another set of parallel grooves (1156) are positioned at a second oblique angle such that grooves (1156) form a criss-cross pattern with grooves (1154). Accordingly, grooves (1154, 1156) may act as a file against tissue positioned between clamp pad (1158) and blade (100) when blade (100) is ultrasonically activated.

Grooves (1154, 1156) may be machined into clamp pad (1158) using a two pass operation and/or using any suitable technique. Other suitable configurations and arrangements for grooves (1056, 1154, 1156) will be apparent to one with ordinary skill in the art in view of the teachings herein. It should also be understood that grooves (1056, 1154, 1156) may be substituted with ridges. As yet another merely illustrative alternative, grooves (1056, 1154, 1156) may be complemented with ridges (e.g., a ridge extending along one or more boundaries of grooves (1056, 1154, 1156), etc.).

B. Exemplary Clamp Pad with Bristles

Figure 34:
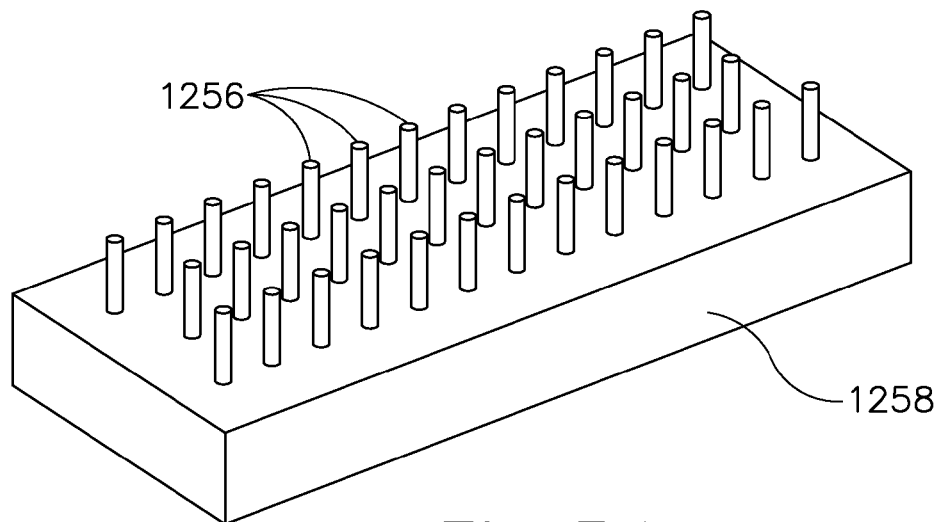
FIG. 34 depicts a perspective view of an exemplary alternative clamp pad with bristles suitable for incorporation with the instrument of FIG. 1.
Figure 35:
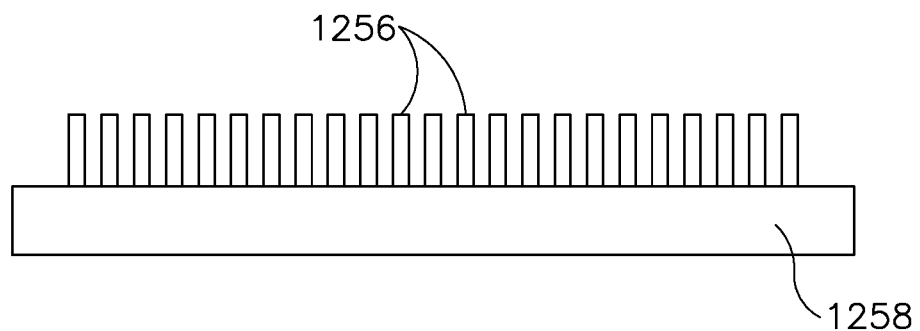
FIG. 35 depicts a side elevational view of the clamp pad of FIG. 34.
Figure 36:
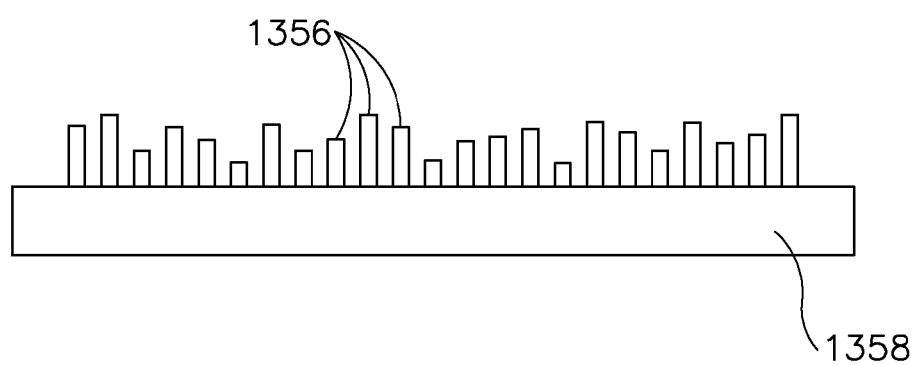
FIG. 36 depicts a side elevational view of an exemplary alternative clamp pad with staggered bristles suitable for incorporation with the instrument of FIG. 1.

FIGS. 34-35 show an exemplary alternative clamp pad (1258) that is similar to clamp pad (58), except that clamp pad (1258) of this example comprises bristles (1256) extending outwardly from clamp pad (1258). Bristles (1256) may be positioned adjacent to blade (100) (and/or tissue) when clamp pad (1258) is assembled within clamp arm (44) of instrument (10) such that bristles (1256) act to help grasp tissue between clamp pad (1258) and blade (100). Bristles (1256) may be formed from a rigid or compliant material. As best seen in FIG. 35, bristles (1256) extend from clamp pad (1258) to an equal height. Alternatively, bristles (1256) may extend from clamp pad (1058) at varying heights. For example, FIG. 36 shows a clamp pad (1358) that is similar to clamp pad (1258), except that clamp pad (1358) includes bristles (1356) that extend at varying heights from clamp pad (1358). Although bristles (1256, 1356) are shown to be laterally and longitudinally aligned with each other, bristles (1256, 1356) may also be misaligned in the lateral and/or longitudinal direction on clamp pad (1258, 1358). In addition or in the alternative, bristles (1256, 1356) may extend at oblique angles from clamp pad (1258, 1358). Other suitable configurations and arrangements for bristles (1256, 1356) will be apparent to one with ordinary skill in the art in view of the teachings herein.

C. Exemplary Clamp Pad with Teeth

Figure 37:
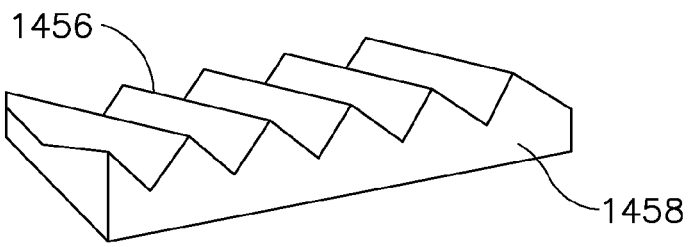
FIG. 37 depicts a perspective view of an exemplary alternative clamp pad with sawteeth suitable for incorporation with the instrument of FIG. 1.
Figure 38:
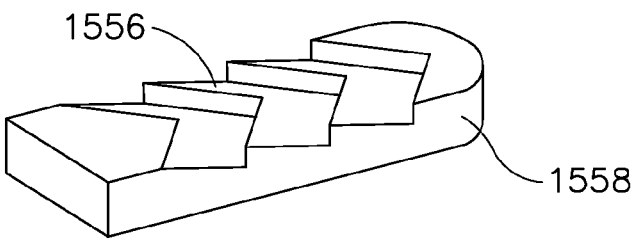
FIG. 38 depicts a perspective view of an exemplary alternative clamp pad with inverted chevron teeth suitable for incorporation with the instrument of FIG. 1.
Figure 39:
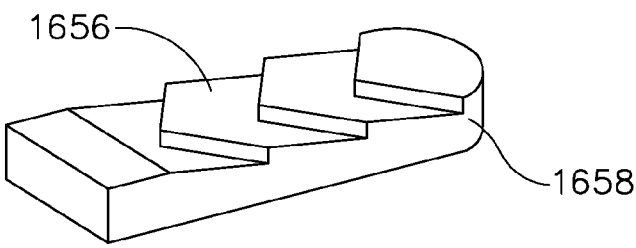
FIG. 39 depicts a perspective view of an exemplary alternative clamp pad with opposing chevron teeth suitable for incorporation with the instrument of FIG. 1.
Figure 40:
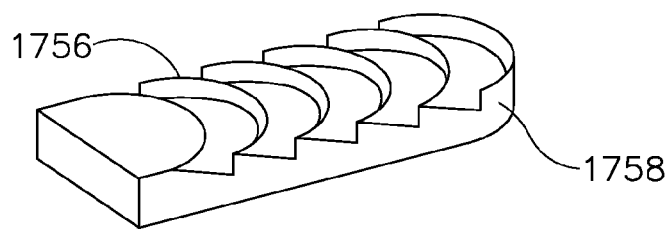
FIG. 40 depicts a perspective view of an exemplary alternative clamp pad with inverted semi-circular teeth suitable for incorporation with the instrument of FIG. 1.
Figure 41:
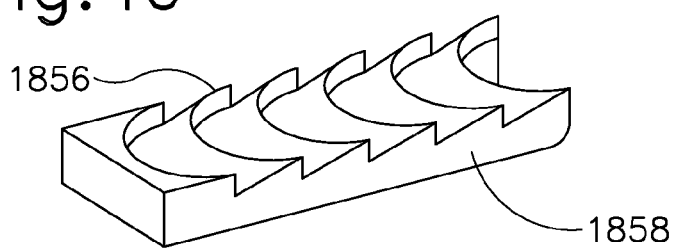
FIG. 41 depicts a perspective view of an exemplary alternative clamp pad with opposing semi-circular teeth suitable for incorporation with the instrument of FIG. 1.

As noted above, the distal portion (58A) of clamp pad (58) includes teeth that have a sawtooth-like configuration, where the teeth extend along paths that are perpendicular to the longitudinal axis of clamp pad (58). Alternatively, teeth on a clamp pad (58) may have various other configurations that may further promote gripping of tissue by clamp pad (58). For example, FIG. 37 shows a clamp pad (1458) that comprises a plurality of teeth (1456) extending transversely across an exterior surface of clamp pad (1458), such that the crests of teeth (1456) extend along paths that are angled obliquely relative to the longitudinal axis of clamp pad (1458). Teeth (1456) protrude outwardly from clamp pad (1458) and may be positioned adjacent to blade (100) and tissue to help in grasping tissue between clamp pad (1458) and blade (100). Of course, teeth (1456) may include other configurations. For example, FIG. 38 shows a clamp pad (1558) that is similar to clamp pad (1458), except that clamp pad (1558) comprises a plurality of teeth (1556) in a chevron configuration pointing in a proximal direction. Teeth (1556) may also point in the opposing direction. For instance, FIG. 39 shows a clamp pad (1658) that is similar to clamp pad (1558), except that teeth (1656) of clamp pad (1658) include a chevron configuration pointing in a distal direction. Alternatively, FIG. 40 shows a clamp pad (1758) that is similar to clamp pad (1558), except that clamp pad (1758) includes teeth (1756) in a semi-circular configuration pointing in a proximal direction. Of course, teeth (1756) may also point in the opposing direction. For instance, FIG. 41 shows a clamp pad (1858) that is similar to clamp pad (1758), except that teeth (1856) of clamp pad (1858) include a semi-circular configuration pointing in a distal direction. Still other suitable tooth configurations will be apparent to one with ordinary skill in the art in view of the teachings herein.

Figure 42:
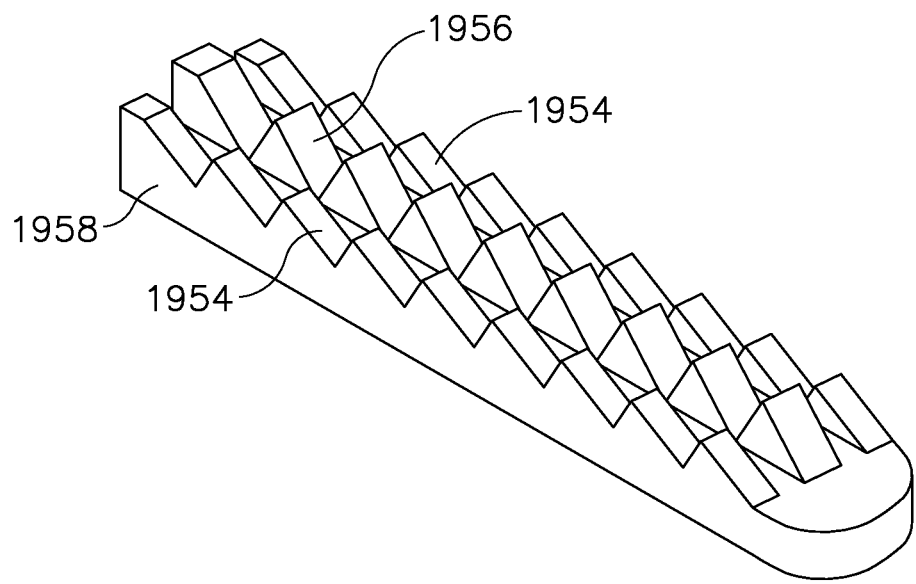
FIG. 42 depicts a perspective view of an exemplary alternative clamp pad with bi-level sawteeth suitable for incorporation with the instrument of FIG. 1.
Figure 43:
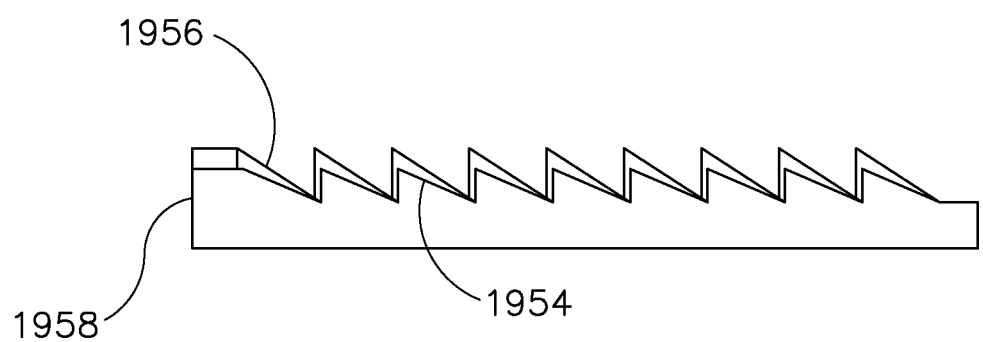
FIG. 43 depicts a side elevational view of the clamp pad of FIG. 42.

FIGS. 42-43 show a clamp pad (1958) that comprises bi-level teeth (1954, 1956). In the present example, clamp pad (1958) comprises a first row of teeth (1956) that extends longitudinally along a central portion of clamp pad (1958). A second and third row of teeth (1954) are positioned laterally along each side of the first row of teeth (1956). The second rows of teeth (1954) extend to a different height than the first row of teeth (1956). As best seen in FIG. 43, teeth (1954) are positioned below teeth (1956). Of course, teeth (1954) may alternatively be positioned above teeth (1956). Teeth (1954, 1956) may therefore be positioned adjacent to blade (100) and tissue to help in grasping tissue between clamp pad (1958) and blade (100). In some versions, teeth (1954) are configured differently from teeth (1956), in addition to or as an alternative to teeth (1954) extending to a different height than teeth (1956). By way of example only, teeth (1954) may have a sawtooth configuration that is oriented proximally while teeth (1956) have a sawtooth configuration that is oriented distally; or vice versa. Other suitable configurations that may be used for teeth (1954, 1956), as well as other suitable relationships between teeth (1954, 1956), will be apparent to one with ordinary skill in the art in view of the teachings herein.

D. Exemplary U-Shaped Clamp Arm

Figure 44:
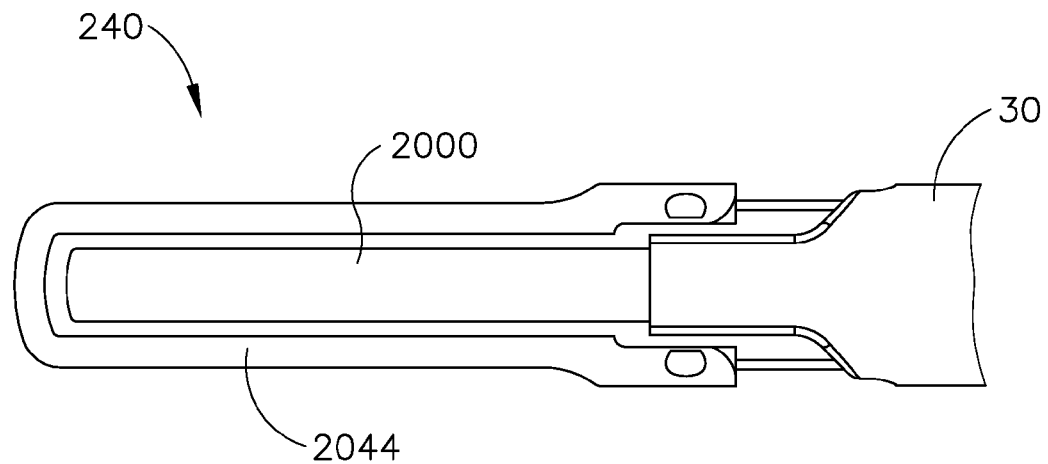
FIG. 44 depicts a top view of an exemplary alternative end effector with a u-shaped clamp arm configuration suitable for incorporation with the instrument of FIG. 1.

In some instances, it may be desirable to provide clamp arm (44) with tissue grasping capabilities without having a feature like clamp pad (58). For instance, FIGS. 44-46 show an end effector (240) that is similar to end effector (40), except that end effector (240) comprises a clamp arm (2044) with a U-shaped configuration. A pivot arm (2048) pivotally secures clamp arm (2044) to shaft assembly (30) and defines an acute angle with clamp arm (2044). As best seen in FIG. 44, clamp arm (2044) is configured to wrap around the lateral sides and distal end of blade (2000). Clamp arm (2044) is further configured to travel past blade (2000) when clamp arm (2044) pivots from an open position to a closed position. In other words, the distal portion of clamp arm (2044) crosses over the longitudinal axis of blade (2000), from one side of the longitudinal axis of blade (2000) to the other side of the longitudinal axis of blade (2000), as clamp arm (2044) pivots from an open position to a closed position.

Figure 45A:
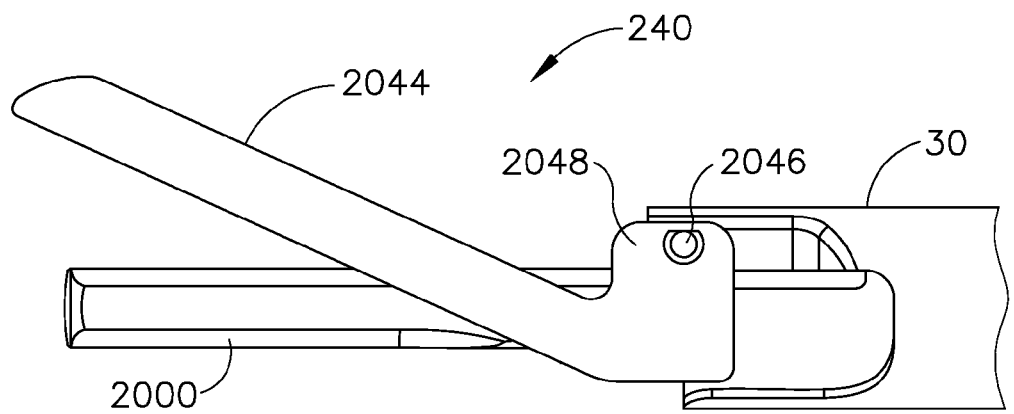
FIG. 45A depicts a side elevational view of the end effector of FIG. 44 in an open configuration.
Figure 45B:
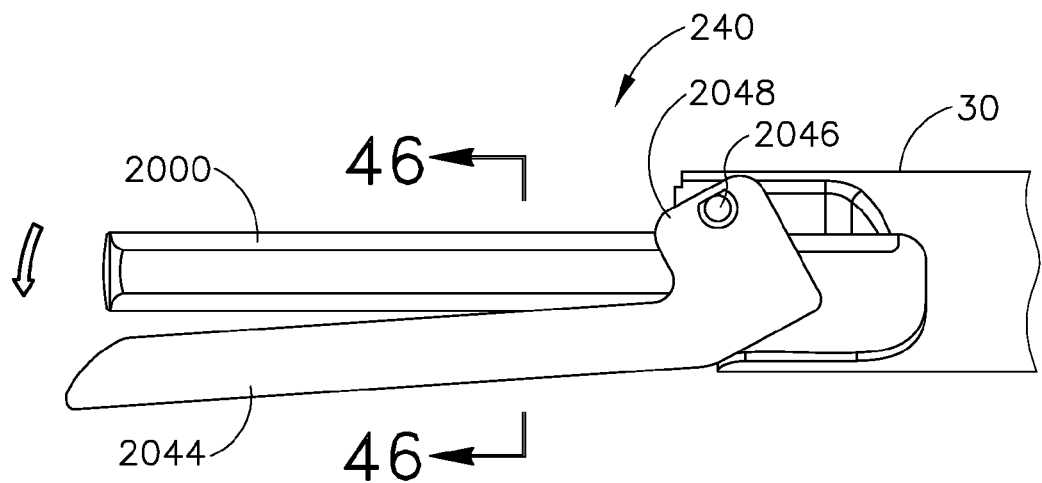
FIG. 45B depicts a side elevational view of the end effector of FIG. 44 in a closed configuration.
Figure 46:
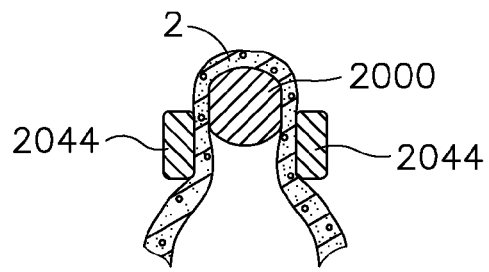
FIG. 46 depicts a cross sectional view of the end effector of FIG. 44 taken along line 46-46 of FIG. 45B, showing tissue clamped within the end effector.

FIG. 45A shows clamp arm (2044) in the open position relative to blade (2000). In the open position, tissue may be positioned between clamp arm (2044) and blade (2000). Trigger (28) may then be actuated to pivot clamp arm (2044) to the closed position shown in FIG. 45B. Clamp arm (2044) pivots around pin (2046) to travel across the longitudinal axis of blade (2000) and past blade (2000). This captures tissue (2) between clamp arm (2044) and blade (2000) to thereby pull tissue (2) over blade (2000), as shown in FIG. 46. This may allow blade (2000) to seal and/or cut tissue (2) in a decreased amount of time. In addition or in the alternative, clamp arm (2044) may provide a shearing action on tissue at both sides of blade (200). Clamp arm (2044) may further allow for advanced hemostasis without pressure on the top side of tissue (2). Other suitable configurations and operabilities for clamp arm (2044) will be apparent to one with ordinary skill in the art in view of the teachings herein.

E. Exemplary Curved Clamp Arm

Figure 47A:
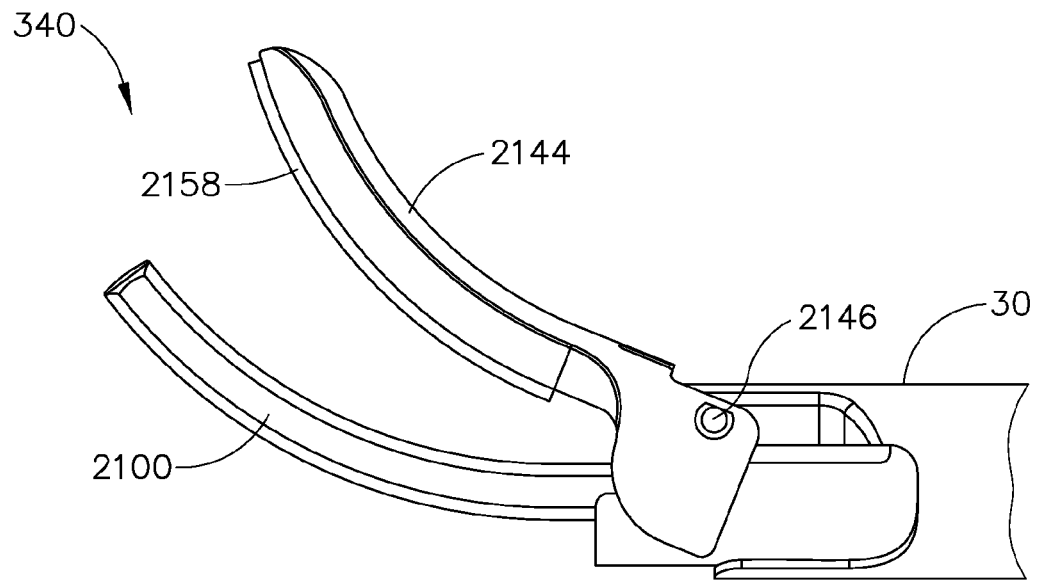
FIG. 47A depicts a side elevational view of an exemplary alternative end effector with a concave configuration suitable for incorporation with the instrument of FIG. 1, in an open configuration.
Figure 47B:
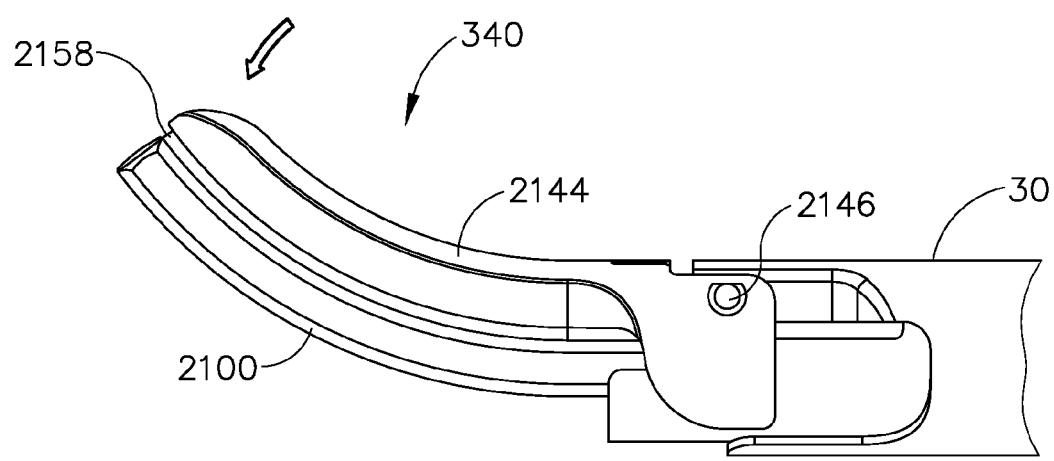
FIG. 47B depicts a side elevational view of the end effector of FIG. 47A in a closed configuration.
Figure 48:
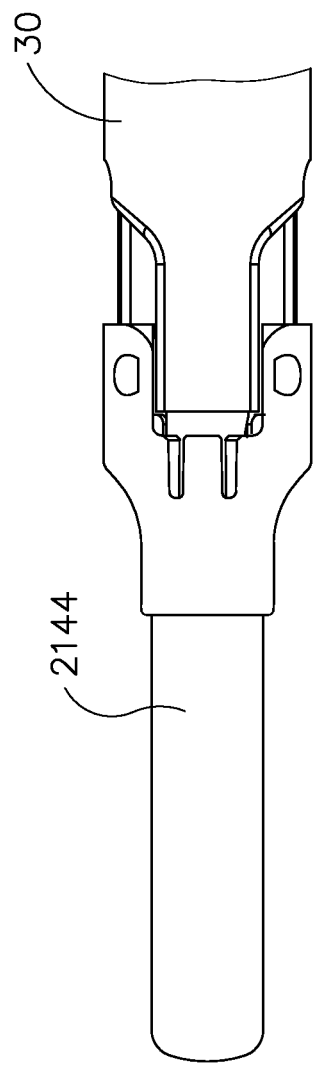
FIG. 48 depicts a top plan view of the end effector of FIG. 47A.

In some versions of instrument (10), clamp arm (44) and blade (100) are both curved along respective planes that are perpendicular to the plane along which clamp arm pivots (44). In some other versions, clamp arm (44) and/or blade (100) is/are curved along a plane or planes that is/are parallel to the plane along which clamp arm (44) pivots. For instance, FIGS. 47A-47B show an end effector (340) that is similar to end effector (40), except that end effector (340) comprises a blade (2100) and clamp arm (2144) with clamp pad (2158) that are all vertically curved along a plane in line with the pivoting motion of clamp arm (2144). FIG. 48 shows a top view of end effector (340), which illustrates that the curvature of clamp arm (2144) is formed such that clamp arm (2144) and blade (2100) both longitudinally extend along planes that are aligned with the longitudinal axis of shaft assembly (30). Referring back to FIGS. 47A-47B, blade (2100) of end effector (340) is curved to correspond to clamp arm (2144) and clamp pad (2158). The curve of blade (2100), clamp arm (2144), and clamp pad (2158) may enable clamp arm (2144) to better grasp tissue between blade (2100) and clamp pad (2158).

FIG. 47A shows clamp arm (2144) in the open position relative to blade (2100). In the open position, tissue may be positioned between clamp pad (2158) and blade (2100). Trigger (28) may then be actuated to pivot clamp arm (2144) to the closed position shown in FIG. 47B. Clamp arm (2144) pivots around pin (2146) to move toward blade (2100). The corresponding curvatures of clamp arm (2144), clamp pad (2158), and blade (2100) act to capture tissue between clamp pad (2158) and blade (2100) to thereby seal and/or cut the tissue. In this example, clamp arm (2144) and clamp pad (2158) are curved convexly relative to the tissue capture region between clamp pad (2158) and blade (2100); while blade (2100) is curved concavely relative to the tissue capture region between clamp pad (2158) and blade (2100).

The curvature of end effector (340) may provide the user with a type of visibility that differs from the visibility provided by end effector (40). The curvature of clamp arm (2144) may further provide for a different form of tissue dissection relative to end effector (40). For example, the top portion of clamp arm (2144) may be pressed against tissue and pulled proximally. The curve of clamp arm (2144) may hold the tissue against clamp arm (2144) to thereby bluntly dissect the tissue as clamp arm (2144) is pulled proximally. Of course, other suitable clamp arm (2144) configurations will be apparent to one with ordinary skill in the art in view of the teachings herein.

Figure 49A:
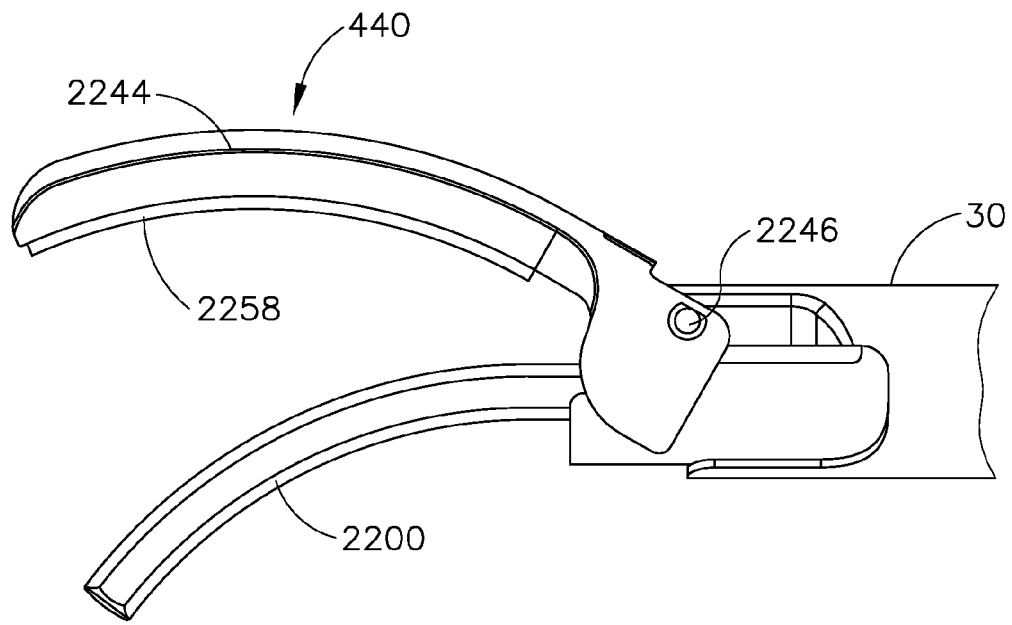
FIG. 49A depicts a side elevational view of an exemplary alternative end effector with a convex configuration suitable for incorporation with the instrument of FIG. 1, in an open configuration.
Figure 49B:
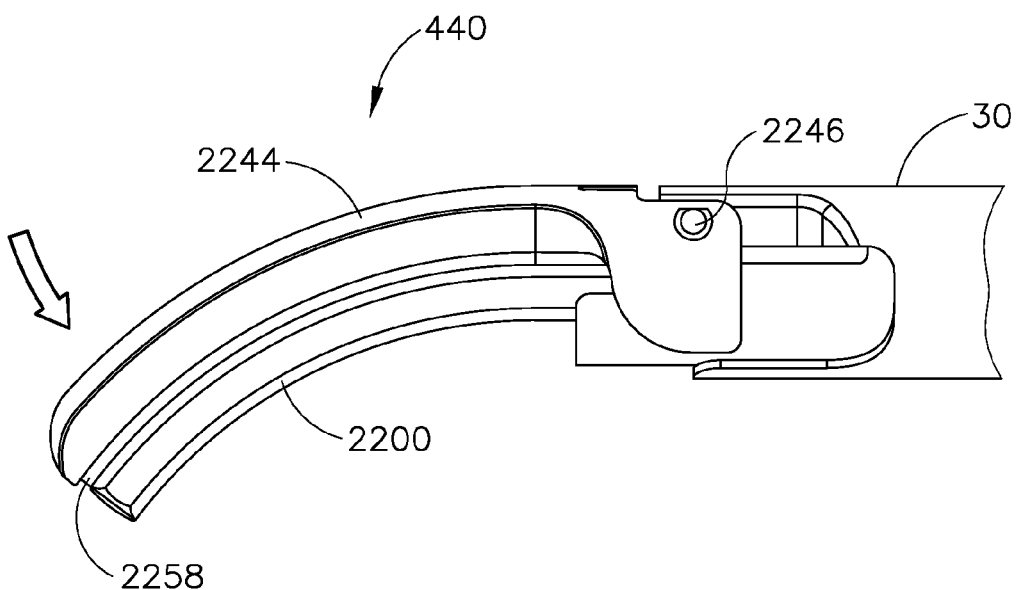
FIG. 49B depicts a side elevational view of the end effector of FIG. 49A in a closed configuration.

FIGS. 49A-49B show another exemplary end effector (440) that is similar to end effector (340), except that clamp arm (2244), clamp pad (2258), and blade (2200) are curved concavely to provide an alternate view of visibility relative to end effector (340). In particular, clamp arm (2244) and clamp pad (2258) are curved concavely relative to the tissue capture region between clamp pad (2258) and blade (2200); while blade (2200) is curved convexly relative to the tissue capture region between clamp pad (2258) and blade (2200). FIG. 49A shows clamp arm (2244) in the open position relative to blade (2200). In the open position, tissue may be positioned between clamp pad (2258) and blade (2200). Trigger (28) may then be actuated to pivot clamp arm (2244) to the closed position shown in FIG. 49B. Clamp arm (2244) pivots around pin (2246) to move toward blade (2200). The corresponding curvatures of clamp arm (2244), clamp pad (2258), and blade (2200) act to capture tissue between clamp pad (2258) and blade (2200) to thereby seal and/or cut the tissue.

F. Exemplary Compliant Clamp Arm

Figure 50A:
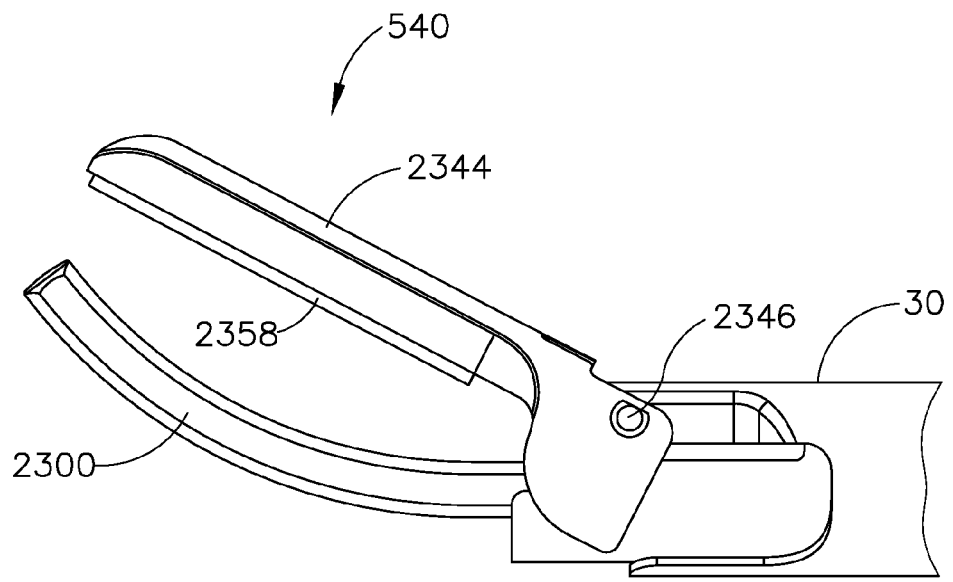
FIG. 50A depicts a side elevational view of an exemplary alternative end effector with a compliant straight clamp arm suitable for incorporation with the instrument of FIG. 1, in an open configuration.
Figure 50B:
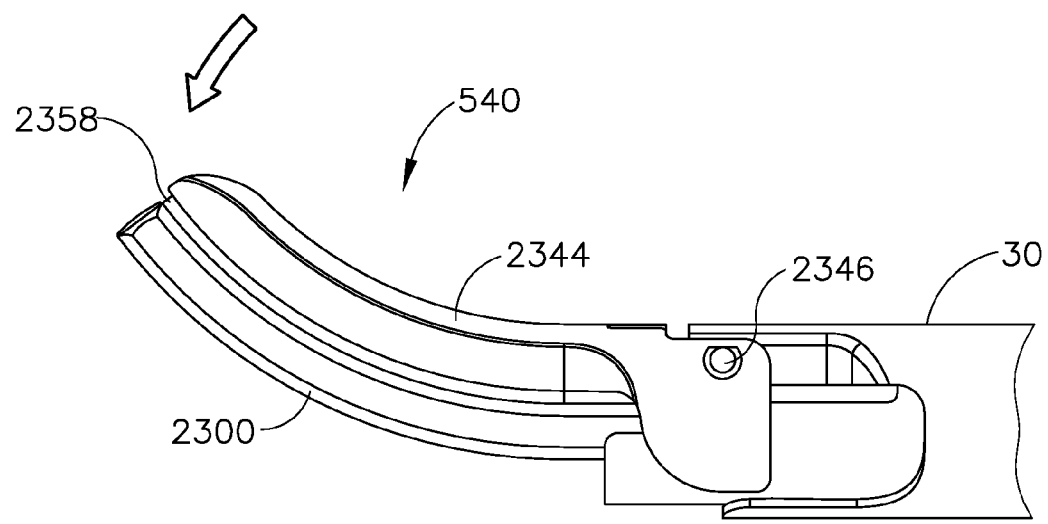
FIG. 50B depicts a side elevational view of the end effector of FIG. 50A in a closed configuration.

FIGS. 50A-50B show an end effector (540) that is similar to end effector (340) in that blade (2300) is curved concavely relative to the tissue capture region between clamp a clamp pad (2358) and blade (2300). In this example, however, clamp arm (2344) and clamp pad (2358) have a straight configuration and are formed of a compliant material. In particular, clamp arm (2344) and clamp pad (2358) are resiliently biased to have a straight configuration as shown in FIG. 50A, which depicts end effector (540) in an open configuration. In this state, tissue may be positioned between clamp arm (2344) and blade (2300). Trigger (28) may then be actuated to pivot clamp arm (2344) to the closed position shown in FIG. 50B. Clamp arm (2344) pivots around pin (2346) to move toward blade (2300). As clamp arm (2344) pivots to the closed position, clamp arm (2344) and clamp pad (2358) bend to correspond to the shape of blade (2300). The distal end of clamp pad (2358) may contact blade (or tissue) first, followed by the proximal region of clamp pad (238) as clamp arm (2344) is pivoted toward the closed position.

The corresponding curvatures of clamp arm (2344), clamp pad (2358), and blade (2300) may act to better grasp tissue between clamp pad (2358) and blade (2300) to thereby seal and/or cut the tissue. By using a compliant clamp arm (2344), the stiffness of blade (2300) may be increased and the pressure profile between clamp pad (2358) and blade (2300) may be optimized to thereby better grasp, seal, and/or cut tissue. A compliant clamp arm (2344) may further compensate for manufacturing variations among parts of end effector (540). Although the present example shows clamp arm (2344) bending convexly to conform to the shape of blade (2300), other suitable compliant configurations for clamp arm (2344) will be apparent to one with ordinary skill in the art in view of the teachings herein.

Figure 51A:
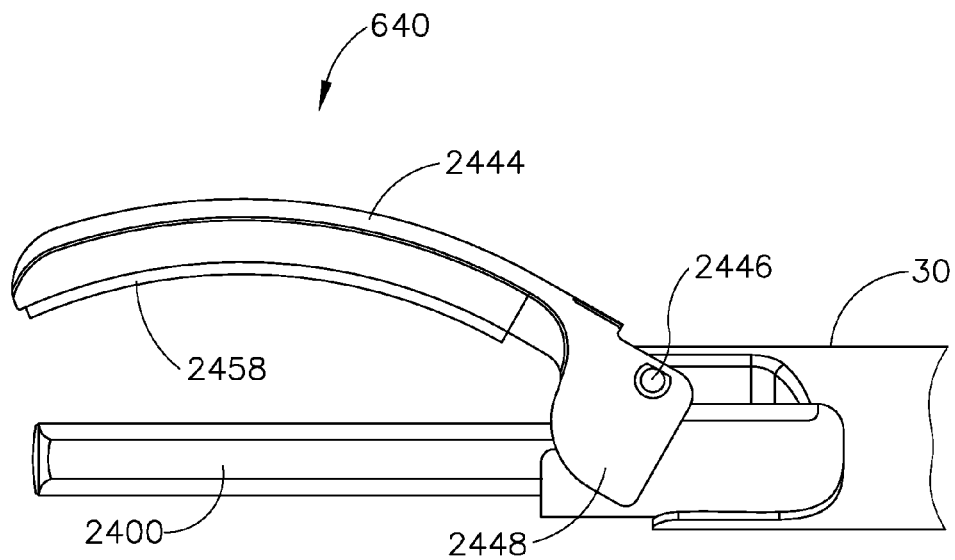
FIG. 51A depicts a side elevational view of an exemplary alternative end effector with a compliant curved clamp arm suitable for incorporation with the instrument of FIG. 1, in an open configuration.
Figure 51B:
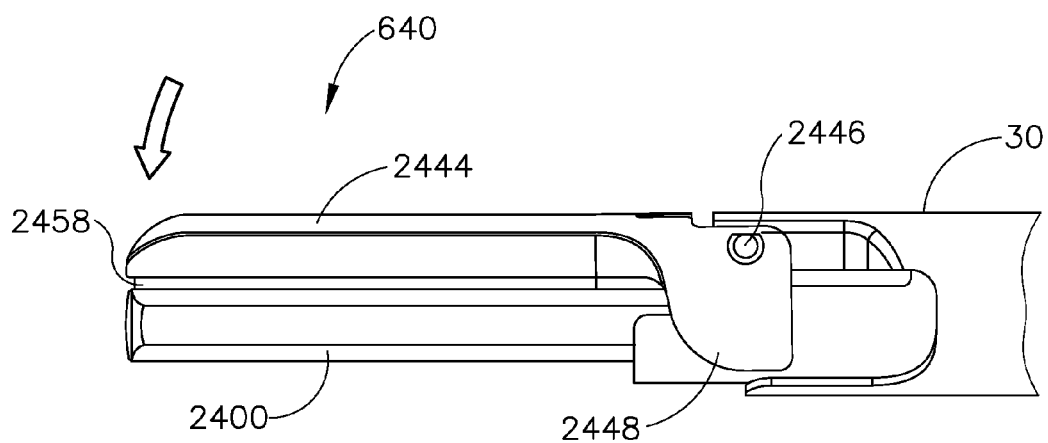
FIG. 51B depicts a side elevational view of the end effector of FIG. 51A in a closed configuration.

FIGS. 51A-51B show an exemplary alternative clamp arm (2444) that bends to a straightened configuration against blade (2400). Clamp arm (2444) and clamp pad (2458) of this example are similar to clamp arm (2344) and clamp pad (2358), except that clamp arm (2444) and clamp pad (2458) are curved concavely relative to the tissue capture region between clamp a clamp pad (2458) and blade (2400) when clamp arm (2444) is in an open position (FIG. 51A). Clamp arm (2444) and clamp pad (2458) may be resiliently biased to assume this curved configuration. Blade (2400) is similar to blade (2300), except that blade (2400) has a straight configuration, such that blade (2400) extends along an axis that is parallel to the longitudinal axis of shaft assembly (30).

Tissue may be positioned between clamp arm (2444) and blade (2400) in this open position as shown in FIG. 51A. Trigger (28) may then be actuated to pivot clamp arm (2444) to the closed position shown in FIG. 51B. Clamp arm (2444) pivots around pin (2446) to move toward blade (2400). As clamp arm (2444) pivots to the closed position, clamp arm (2444) and clamp pad (2458) bend to correspond to the straight configuration of blade (2400). The corresponding shapes of clamp arm (2444), clamp pad (2458), and blade (2400) may act to better grasp tissue between clamp pad (2458) and blade (2400) to thereby seal and/or cut the tissue.

Figure 52:
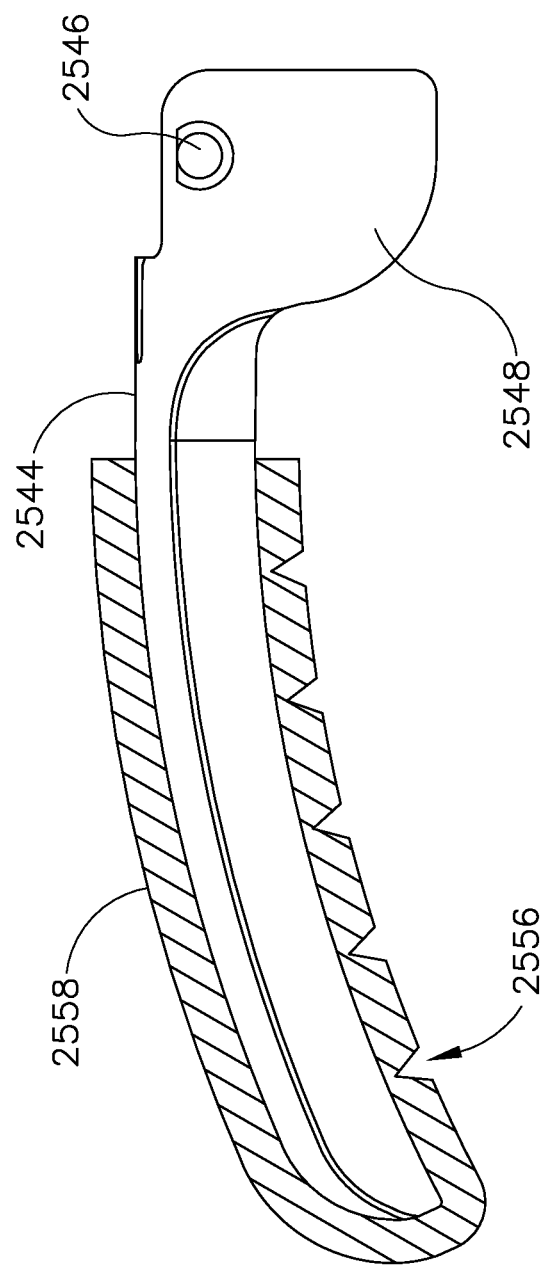
FIG. 52 depicts a cross sectional view of an exemplary alternative clamp arm with an overmolded clamp pad for use with the end effector of FIG. 51A.

To be compliant, spine (2448) of clamp arm (2444) may be formed from a compliant material to flex with blade (2400), while the distal portion of clamp arm (2444) may be more rigid than spine (2448). Spine (2448) may allow clamp arm (2444) to flatten and provide closure between both the distal and proximal portions of clamp arm (2444) with blade (2400). Of course, other suitable compliant configurations will be apparent to one with ordinary skill in the art. For instance, FIG. 52 shows a clamp arm (2544) that is similar to clamp arm (2444), except that clamp arm (2544) comprises an overmolded clamp pad (2558). To allow clamp pad (2558) to flex with clamp arm (2544), clamp pad (2558) defines recesses (2556) in the overmold. While four recesses (2556) are shown in FIG. 52, any other suitable number of recesses (2556) may be used to allow for sufficient flexing of overmolded clamp pad (2558). Accordingly, recesses (2556) may flex to a wider configuration when clamp arm (2544) flexes to the closed position against blade (2400) to thereby allow clamp pad (2558) to flex with clamp arm (2544).

Figure 53:
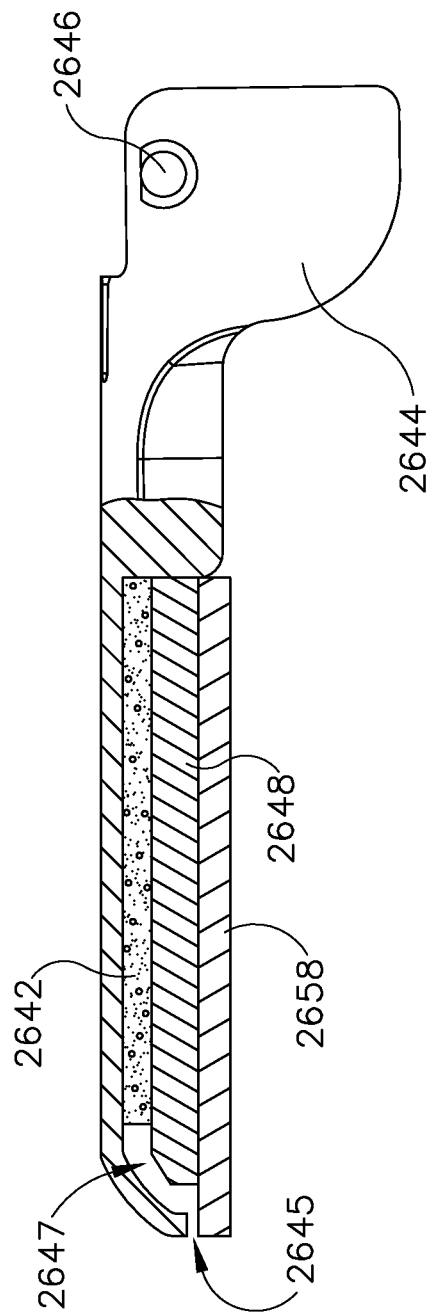
FIG. 53 depicts a cross sectional view of an exemplary alternative clamp arm with a compliant material for use with the end effector of FIG. 51A

FIG. 53 shows an exemplary clamp arm (2644) comprising a compliant foam portion (2642). Clamp arm (2644) is similar to clamp arm (2444), except that clamp arm (2644) includes a recess (2647) and a block member (2648). Foam portion (2642) is positioned within recess (2647) of clamp arm (2644). Block member (2648) is interposed between clamp pad (2658) and foam portion (2642). Foam portion (2642) is resiliently biased to assume an expanded configuration, such that foam portion (2642) urges clamp pad (2658) away from clamp arm (2444). When tissue is not being compressed between clamp pad (2658) and ultrasonic blade (100), a gap (2645) is defined between clamp arm (2444) and clamp pad (2658) due to the resilient bias imposed by foam portion (2642). However, when tissue is compressed between clamp pad (2658) and ultrasonic blade (100), foam portion (2648) also compresses, reducing the size of gap (2645) or even eliminating gap (2645). In some instances, tissue between clamp pad (2658) and ultrasonic blade (100) does not extend along the full length of clamp pad (2658) and ultrasonic blade (100). Compliance in foam portion (2642) may accommodate this uneven thickness along the length of the interface between clamp pad (2658) and ultrasonic blade (100); and may further provide a substantially even distribution of compression force along the length of tissue interposed between clamp pad (2658) and ultrasonic blade (100).

Figure 54:
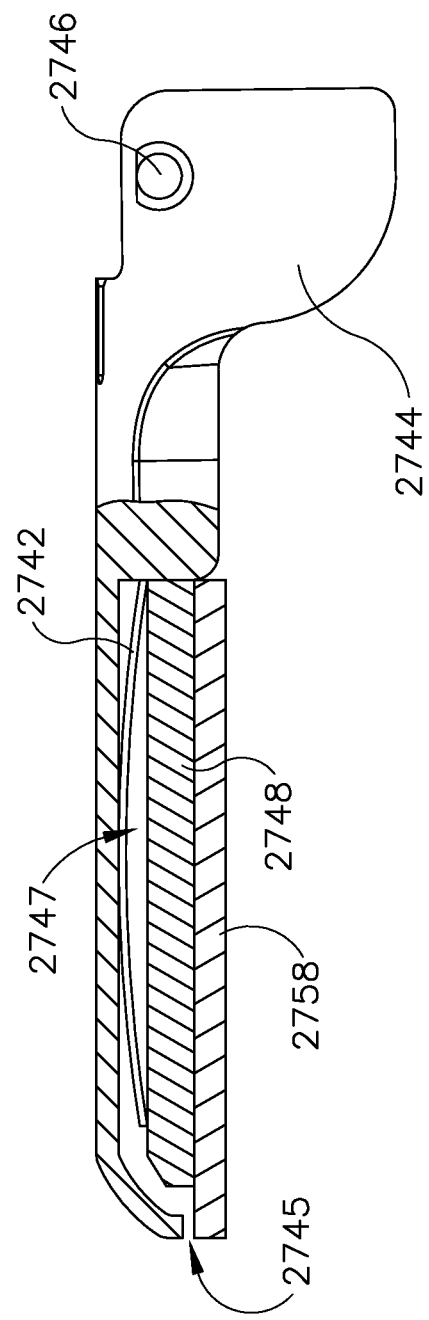
FIG. 54 depicts a cross sectional view of an exemplary alternative clamp arm with a resilient member for use with the end effector of FIG. 51A.

FIG. 54 shows an exemplary clamp arm (2744) comprising a leaf spring (2742). Clamp arm (2744) is similar to clamp arm (2644), except that clamp arm (2744) includes leaf spring (2742) instead of foam portion (2642). Leaf spring (2742) is positioned within recess (2747) of clamp arm (2744). Block member (2748) is interposed between clamp pad (2758) and leaf spring (2742). Leaf spring (2742) is resiliently biased to urge clamp pad (2758) away from clamp arm (2444). When tissue is not being compressed between clamp pad (2758) and ultrasonic blade (100), a gap (2745) is defined between clamp arm (2444) and clamp pad (2758) due to the resilient bias imposed by leaf spring (2742). However, when tissue is compressed between clamp pad (2758) and ultrasonic blade (100), leaf spring (2748) deforms to reduce the size of gap (2745) or even eliminating gap (2745). In some instances, tissue between clamp pad (2758) and ultrasonic blade (100) does not extend along the full length of clamp pad (2758) and ultrasonic blade (100). Compliance in leaf spring (2742) may accommodate this uneven thickness along the length of the interface between clamp pad (2758) and ultrasonic blade (100); and may further provide a substantially even distribution of compression force along the length of tissue interposed between clamp pad (2758) and ultrasonic blade (100).

IV. Exemplary Clamp Arm with Blunt Dissection Features

The above examples are mainly described in the context of compressing tissue between a clamp pad (58) and ultrasonic blade (100). However, in some instances it may be desirable to use instrument (10) to perform a blunt dissection of tissue without necessarily capturing tissue between clamp pad (58) and ultrasonic blade (100) to sever/seal the tissue. For instance, end effector (40) may be inserted between two layers of tissue while clamp arm (44) is in a closed position, and then clamp arm (44) may be driven to the open position to separate the layers of tissue. Alternatively, with blade (100) in an inactive state, an outer surface of clamp arm (44) may be pressed against tissue and/or dragged against tissue to drive one tissue structure apart from another tissue structure. Accordingly, end effector (40) may be provided with one or more features that are configured to facilitate blunt dissection or additional methods of tissue dissection. The following are merely illustrative examples of blunt dissection features that may be readily incorporated into end effector (40). Other suitable blunt dissection features will be apparent to one with ordinary skill in the art in view of the teachings herein.

Figure 55A:
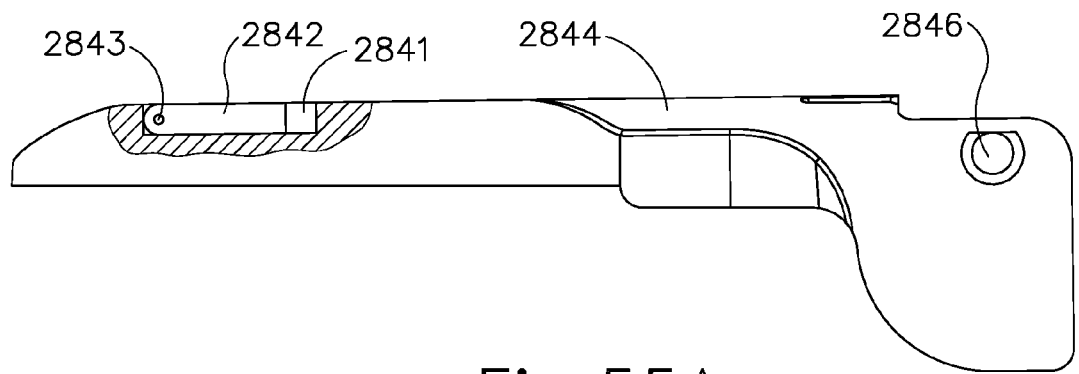
FIG. 55A depicts a cross sectional view of an exemplary alternative clamp arm with a blunt dissection feature suitable for incorporation with the instrument of FIG. 1, showing the blunt dissection feature in a stowed position.
Figure 55B:
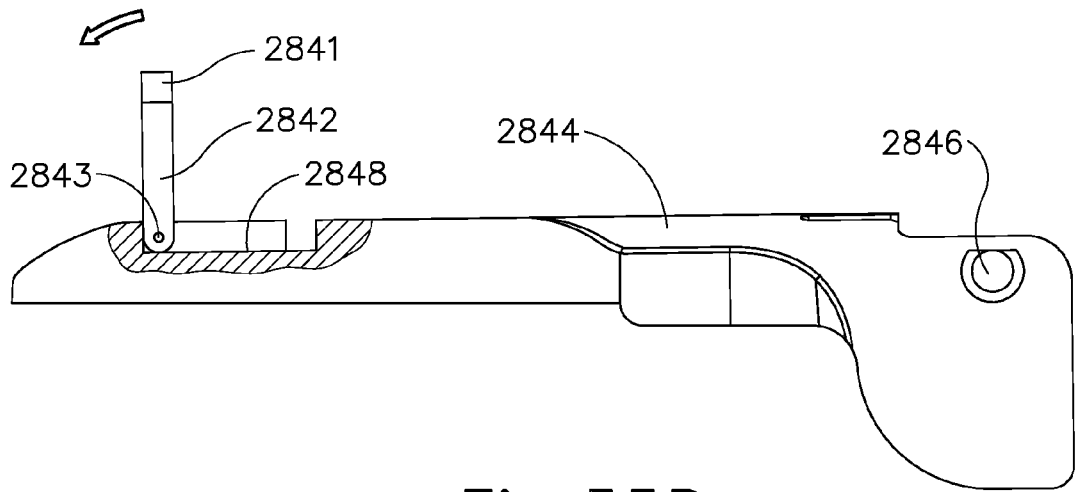
FIG. 55B depicts a cross sectional view of the clamp arm of FIG. 55A, showing the blunt dissection feature in a deployed position.
Figure 56:
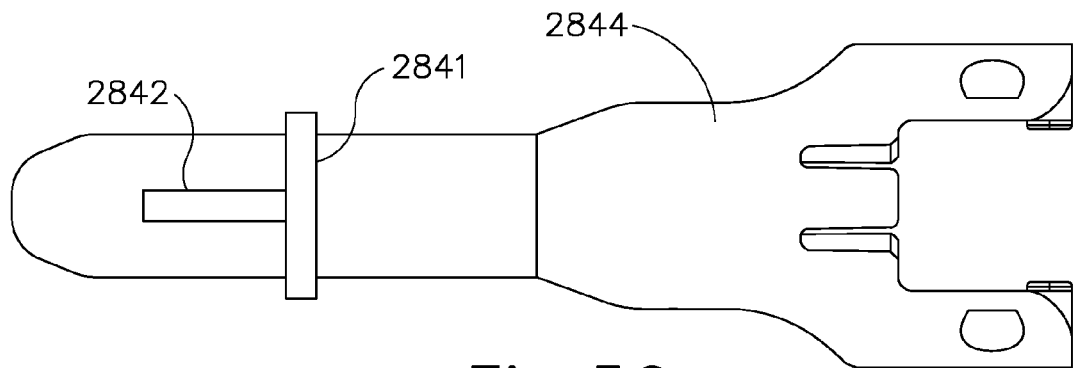
FIG. 56 depicts a top plan view of the clamp arm of FIG. 55A, showing the blunt dissection feature in the stowed position.

FIGS. 55A-56 show a clamp arm (2844) that is similar to clamp arm (44), except that clamp arm (2844) of this example comprises a pivoting dissection arm (2842) that may be used to bluntly dissect tissue. It should be understood that clamp arm (2844) may have a clamp pad, including but not limited to any of the various clamp pads described herein. As best seen in FIG. 56, arm (2842) has a T-shaped configuration with a bar (2842) extending transversely from clamp arm (2844). Arm (2842) is positioned on a distal portion of clamp arm (2844) and is pivotable relative to clamp arm (2844) via pin (2843).

Arm (2842) may be positioned against clamp arm (2844) in a stowed position, as shown in FIG. 55A, while clamp arm (2844) is being introduced to the surgical site and when end effector (40) is being used to seal/sever tissue clamped between clamp arm (2844) and blade (100). The present example shows arm (2842) being substantially flush with clamp arm (2844) in the stowed position. Alternatively, arm (2842) may be positioned above clamp arm (2844). When a blunt tissue dissection is desired, arm (2842) may be raised and pivoted away from clamp arm (2844), as shown in FIG. 55B. In the present example, bar (2841) of arm (2842) extends beyond clamp arm (2844), as shown in FIG. 56, to allow a user to grasp bar (2841) (e.g., using another instrument) to raise arm (2842). As another merely illustrative example, a free end of bar (2841) may be dragged against tissue to pivot arm (2842) to the deployed position. Other suitable methods for raising arm (2842) relative to clamp arm (2844) will be apparent to one with ordinary skill in the art in view of the teachings herein.

Figure 57:
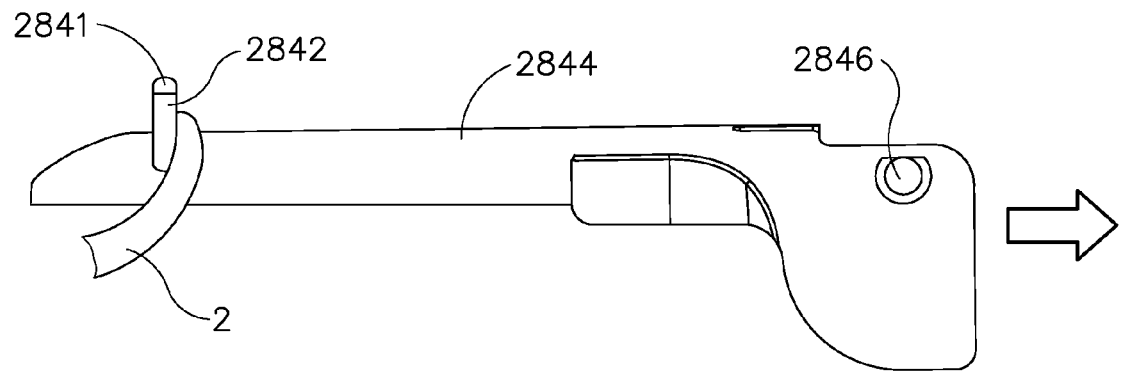
FIG. 57 depicts a side elevational view of the clamp arm of FIG. 55A, showing the blunt dissection feature performing a blunt dissection of tissue.
Figure 58:
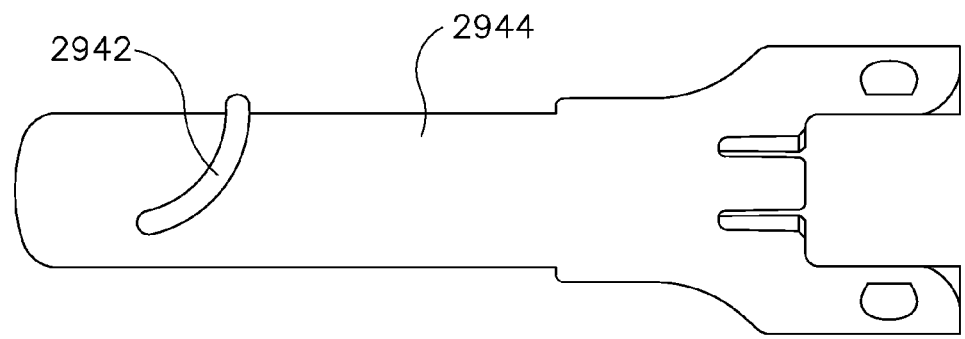
FIG. 58 depicts a top view of an exemplary alternative clamp arm with a curved blunt dissection feature suitable for incorporation with the instrument of FIG. 1, with the blunt dissection feature in a stowed position.
Figure 59:
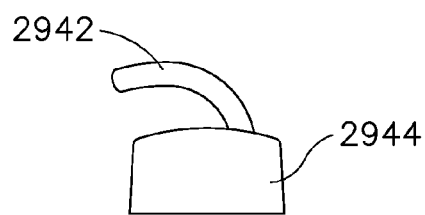
FIG. 59 depicts a front end view of the clamp arm of FIG. 58, with the blunt dissection feature in a deployed position.

With arm (2842) in the raised position, tissue (2) may be positioned around a proximal side of arm (2842), as shown in FIG. 57. Clamp arm (2844) may then be pulled proximally to dissect tissue (2) with arm (2842). The T-shaped configuration of arm (2842) holds tissue (2) against arm (2842) during the dissection. Of course, arm (2842) may include other suitable configurations for holding tissue (2) on arm (2842). For instance, FIGS. 58-59 show a clamp arm (2944) having an arm (2942) with a curved hook-like configuration. Arm (2942) is similar to arm (2842), except that arm (2942) curves proximally and laterally along clamp arm (2944). As best seen in FIG. 58, arm (2942) extends past the lateral side of clamp arm (2944) to allow a user to grasp arm (2942) to pivot arm (2942) relative to clamp arm (2944). In the raised or deployed position, as shown in FIG. 59, arm (2942) may be used to hook tissue around arm (2942) to bluntly dissect the tissue. Other suitable configurations and operabilities that may be used and provided for arm (2842, 2942) will be apparent to one with ordinary skill in the art in view of the teachings herein.

Figure 60:
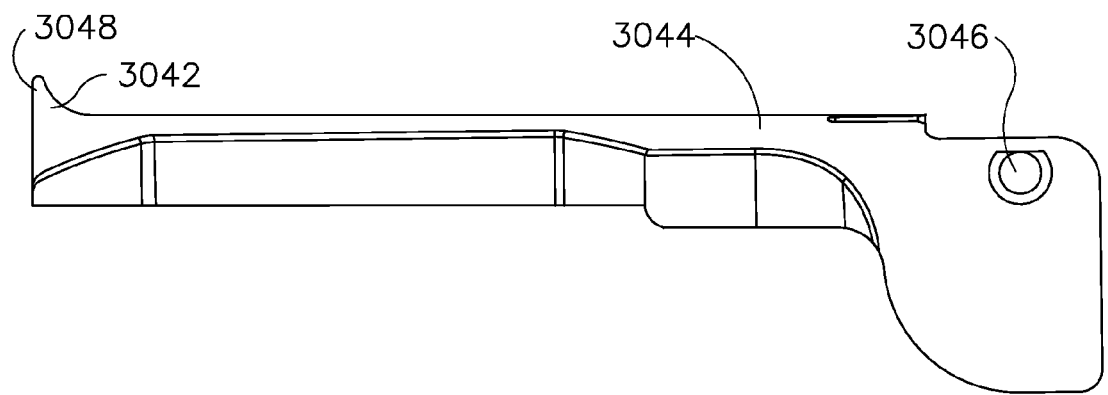
FIG. 60 depicts a side elevational view of an exemplary alternative clamp arm with a protrusion suitable for incorporation with the instrument of FIG. 1.

In some instances, it may be desirable to bluntly dissect tissue without raising an arm (2842, 2942). FIG. 60 shows an exemplary alternative clamp arm (3044) that may be used to bluntly dissect tissue. Clamp arm (3044) is similar to clamp arm (2844), except that clamp arm (3044) comprises a unitary protrusion (3048) on a distal portion of clamp arm (3044) instead of an arm (2842). Protrusion (3048) extends outwardly from clamp arm (3044) and includes a proximal surface (3042). Accordingly, protrusion (3048) may be pressed against tissue and pulled proximally such that proximal surface (3042) acts to perform a blunt dissection of the tissue. In settings where clamp arm (3044) is used to provide a spreading dissection by separating layers of tissue from each other, protrusion (3048) may assist with gripping one of the layers of tissue to thereby prevent the layer of tissue from slipping off of the distal end of clamp arm (3044).

Figure 61:
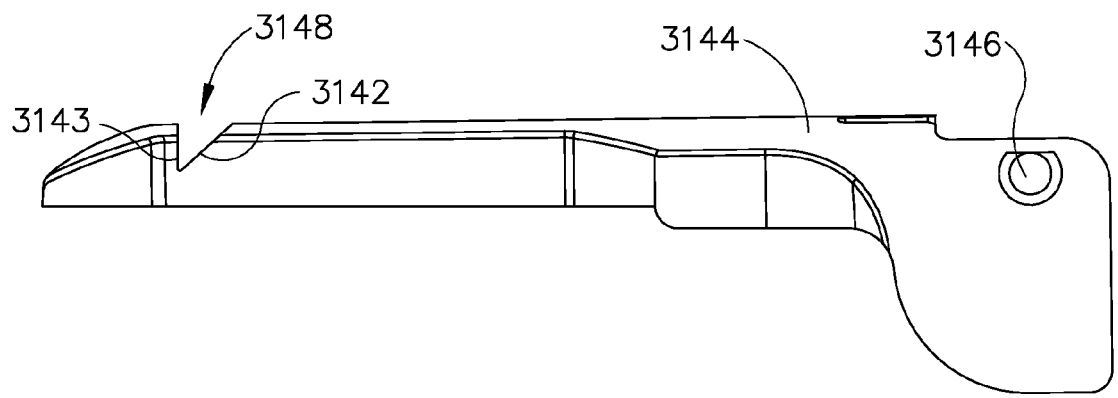
FIG. 61 depicts a side elevational view of an exemplary alternative clamp arm with a recess suitable for incorporation with the instrument of FIG. 1.

In another exemplary variation as shown in FIG. 61, a clamp arm (3144) that is similar to clamp arm (3044) defines a recess (3148) on a distal portion of clamp arm (3144). Recess (3148) includes a distal surface (3143) and a proximal surface (3142). In the present example, distal surface (3143) is vertically aligned in clamp arm (3144) and proximal surface (3142) slopes distally to distal surface (3143). Of course, other suitable configurations for recess (3148) will be apparent to one with ordinary skill in the art in view of the teachings herein. In the present example, the distal portion of clamp arm (3144) may be pressed against tissue and pulled proximally such that the tissue may slide against proximal surface (3142) to distal surface (3143). Distal surface (3143) may then engage the tissue to perform a blunt dissection of the tissue. In settings where clamp arm (3144) is used to provide a spreading dissection by separating layers of tissue from each other, recess (3148) may assist with gripping one of the layers of tissue to thereby prevent the layer of tissue from slipping off of the distal end of clamp arm (3144). Other suitable clamp arm (3044, 3144) features for bluntly dissection tissue will be apparent to one with ordinary skill in the art in view of the teachings herein.

V. Exemplary Clamp Arm with Porous Coating

Figure 62A:
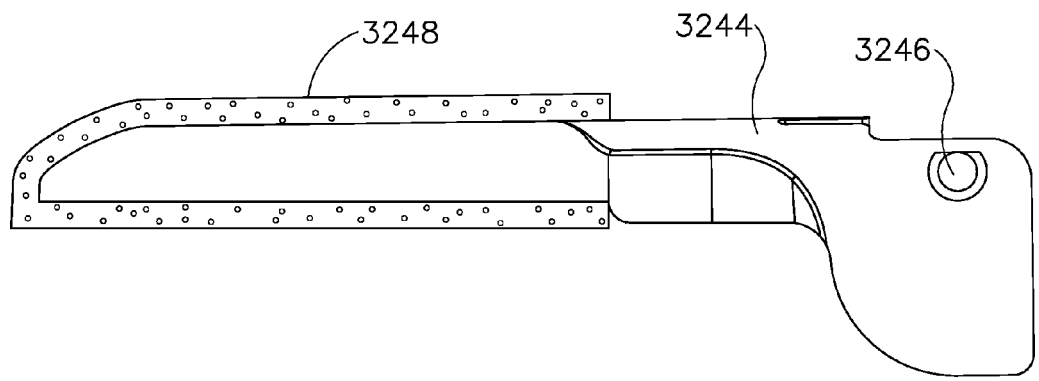
FIG. 62A depicts a cross sectional view of an exemplary alternative clamp arm with a coating suitable for incorporation with the instrument of FIG. 1, showing the coating in a unfilled state.
Figure 62B:
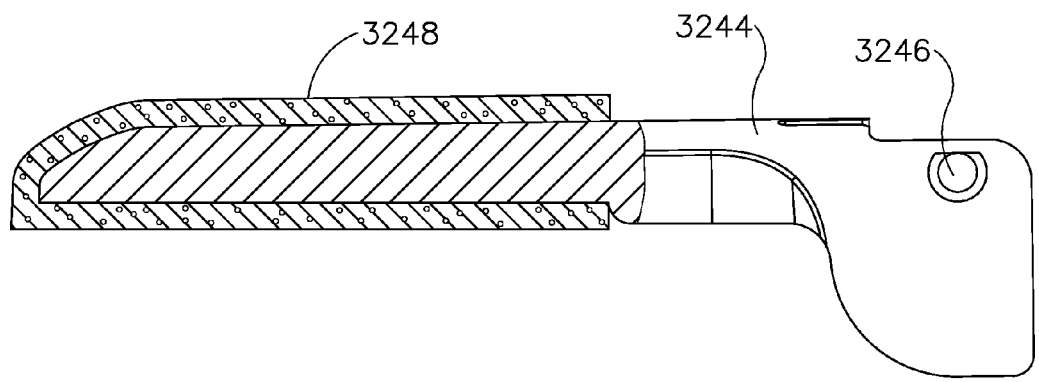
FIG. 62B depicts a cross sectional view of the clamp arm of FIG. 64A, showing the coating in a filled state.

In some instances, it may be desirable coat clamp arm (44) with a porous coating. An example of such a porous coating is disclosed in U.S. Pat. No. 4,526,839, entitled "Process for Thermally Spraying Porous Metal Coatings on Substrates," issued Jul. 2, 1985, the disclosure of which is incorporated by reference herein. FIGS. 62A-62B show a clamp arm (3244), which is similar to clamp arm (44), except that clamp arm (3244) comprises a coating (3248) applied to the distal portion of clamp arm (3244). Coating (3248) may be a porous material, such as a metal, ceramic, etc. If a ceramic material is used in coating (3248), coating (3248) may act as an insulative layer by allowing air to reside in the pores of coating (3248), as shown in FIG. 62A, to help with the heat management of clamp arm (3244). In other words, coating (3248) may provide thermal insulation of clamp arm (3244).

When clamp arm (3244) is used within a patient, bodily fluids may penetrate coating (3248) and migrate into the pores of coating (3248), as shown in FIG. 62B. This may provide an additional cooling effect as the fluids evaporate off of clamp arm (3244), which may prevent the exterior of clamp arm (3244) from overheating. For instance, coating (3248) may prevent the exterior of clamp arm (3244) from exceeding 100° C. until the fluids are evaporated from clamp arm (3244). Since these bodily fluids, which may include blood, may have a different appearance than coating (3248), the fluids may change the color and/or appearance of coating (3248) when the fluids are absorbed by coating (3248). This may provide a visual indication that clamp arm (3244) has been used, as shown in FIG. 62B. It should be understood that the pore size of coating (3248) may effect the ease of removing these fluids from coating (3248). Suitable pore sizes may be selected by the user.

Coating (3248) of the present example is applied circumferentially around clamp arm (3244). Alternatively, coating (3248) may be applied to selected areas of clamp arm (3248), such as the top surface of clamp arm (3248), or other areas of instrument (10). It should also be understood that the underside of clamp arm (3244) may include a clamp pad similar to clamp pad (58). Coating (3248) may be absent from such a clamp pad, such that a tissue contacting surface of the clamp pad is exposed relative to clamp arm (3244) and relative to coating (3248). Other suitable configurations for coating (3248) will be apparent to one with ordinary skill in the art in view of the teachings herein.

Although coating (3248) has been described for a clamp arm (3244) of an ultrasonic instrument (10), it should be noted that coating (3248) could also be incorporated into other instruments. For example, coating (3248) may be added to end effectors of RF electrosurgical devices, surgical stapling devices, and/or other suitable surgical instruments. By way of example only, surgical instrument (10) may comprise an electrosurgical instrument constructed in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218; U.S. Pub. No. 2012/0116379; U.S. Pub. No. 2012/0078243; U.S. Pub. No. 2012/0078247; U.S. patent application Ser. Nos. 13/622,729; 13/622,735; and/or 13/658,784. The disclosures of each of the foregoing references are incorporated by reference herein. Alternatively, surgical instrument (10) may comprise a surgical stapling and cutting instrument constructed in accordance with at least some of the teachings of U.S. Pat. No. 7,416,101; U.S. Pub. No. 2009/0209990; U.S. Pub. No. 2012/0239012; and/or U.S. patent application Ser. No. 13/716,308. The disclosures of each of the foregoing references are incorporated by reference herein.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising an end effector, wherein the end effector comprises:
   (a) an ultrasonic blade, wherein the end effector is operable to apply ultrasonic energy at the blade;
   (b) a clamp arm pivotable relative to the blade; and
   (c) a clamp pad secured to the clamp arm, wherein the clamp pad is positioned to oppose the blade such that the end effector is operable to compress tissue between the clamp pad and the blade;
   wherein the clamp arm comprises a latching feature operable to retain the clamp pad relative to the clamp arm, wherein the latching feature is operable to prevent the clamp pad from moving laterally, longitudinally, and perpendicularly relative to the clamp arm, wherein the latching feature comprises a carrier wrapped around a portion of the clamp pad such that the clamp pad is positioned within the carrier, wherein the carrier is positioned within the clamp arm, wherein the carrier comprises a protrusion, wherein the clamp arm comprises a slot, wherein the protrusion of the carrier is disposed in the slot of the clamp arm.

2. The apparatus of claim 1, wherein the latching feature further comprises a plurality of barbs extending from the clamp arm, wherein the barbs are configured to engage the clamp pad.

3. The apparatus of claim 1, wherein the latching feature further comprises at least one groove extending laterally into an interior sidewall of the clamp arm, wherein the clamp pad comprises a sidewall having at least one laterally extending protrusion disposed within the groove of the clamp arm.

4. The apparatus of claim 1, wherein the clamp arm defines an opening, wherein the clamp pad defines an indentation that is configured to align with the opening of the clamp arm, wherein the latching feature further comprises a fastener inserted within the opening of the clamp arm to engage the indentation of the clamp pad.

5. The apparatus of claim 1, wherein the clamp arm comprises a porous coating.

6. The apparatus of claim 1, wherein the clamp pad comprises a plurality of grooves.

7. The apparatus of claim 6, wherein the grooves are arranged in a criss-cross pattern.

8. The apparatus of claim 1, wherein the clamp pad comprises a plurality of bristles.

9. The apparatus of claim 1, wherein the clamp pad comprises a plurality of teeth in a chevron configuration.

10. The apparatus of claim 1, wherein the clamp pad comprises a plurality of teeth in a semi-circular configuration.

11. The apparatus of claim 1, wherein the clamp pad has a first set of teeth and a second set of teeth, wherein the teeth of the first set extend to a first height, wherein the teeth of the second set extend to a second height, wherein the first height is greater than the second height.

12. The apparatus of claim 1, wherein the clamp arm is pivotable relative to the blade along a pivot plane, wherein one or both of the clamp arm or the blade is curved along the pivot plane.

13. The apparatus of claim 1, wherein the clamp arm has a distal end, wherein the clamp pad is located at one side of the distal end of the clam arm, wherein the other side of the distal end of the clamp arm includes a blunt dissection feature, wherein the blunt dissection feature protrudes from or is recessed relative to an outer surface of the clamp arm.

14. The apparatus of claim 13, wherein the blunt dissection feature is pivotable relative to the clamp arm between a stowed position and a deployed position.

15. An apparatus for operating of tissue, the apparatus comprising an end effector, wherein the end effector comprises:

(a) an ultrasonic blade, wherein the end effector is operable to apply ultrasonic energy at the blade;

(b) a clamp arm pivotable relative to the blade, wherein the clamp arm comprises a latching feature; and (c) a clamp pad configured to be selectively secured to the clamp arm; wherein the clamp pad is positioned to oppose the blade when the clamp pad is secured to the clamp arm such that the end effector is operable to compress tissue between the clamp pad and the blade; wherein the latching feature is operable to prevent the clamp pad from moving laterally, longitudinally, and perpendicularly relative to the clamp arm when the clamp pad is secured to the clamp arm, wherein the latching feature comprises a plurality of barbs, wherein the clamp pad comprises a plurality of openings configured to receive the plurality of barbs.

16. The apparatus of claim 15, wherein the latching feature defines a recess and the plurality of barbs extend from the recess.

17. An apparatus for operating on tissue, the apparatus comprising an end effector, wherein the end effector comprises:

(a) an ultrasonic blade, wherein the end effector is operable to apply ultrasonic energy at the blade;

(b) a clamp arm pivotable relative to the blade; and (c) a clamp pad secured to the clamp arm such that the clamp pad is prevented from moving laterally, longitudinally, and perpendicularly relative to the clamp arm, wherein the clamp pad is positioned to oppose the blade such that the end effector is operable to compress tissue between the clamp pad and the blade;

wherein the clamp arm has a distal end, wherein the clamp pad is located at one side of the distal end of the clam arm, wherein the other side of the distal end of the clamp arm includes a blunt dissection feature, wherein the blunt dissection feature protrudes from or is recessed relative to an outer surface of the clamp arm;

wherein the blunt dissection feature is pivotable relative to the clamp arm between a stowed position and a deployed position.

\* \* \* \* \*